United States Patent
Fenton et al.

(10) Patent No.: US 6,762,199 B2
(45) Date of Patent: Jul. 13, 2004

(54) INDANE DERIVATIVES

(75) Inventors: Garry Fenton, West Malling (GB);
Clive McCarthy, West Malling (GB);
Robert Edward MacKenzie, West Malling (GB); Andrew David Morley, West Malling (GB)

(73) Assignee: Aventis Pharma Limited, Kent (GB)

( * ) Notice: Subject to any disclaimer, the term of this patent is extended or adjusted under 35 U.S.C. 154(b) by 0 days.

(21) Appl. No.: 10/229,592

(22) Filed: Aug. 28, 2002

(65) Prior Publication Data
US 2003/0199564 A1 Oct. 23, 2003

Related U.S. Application Data

(63) Continuation of application No. PCT/GB01/00844, filed on Feb. 28, 2001.

(30) Foreign Application Priority Data
Feb. 28, 2000 (GB) .............................................. 0004686

(51) Int. Cl.$^7$ ..................... A61K 31/423; C07D 263/54
(52) U.S. Cl. ........................ 514/375; 548/217; 548/237; 514/377
(58) Field of Search ................................ 548/217, 237, 548/222; 514/375, 377

(56) References Cited

FOREIGN PATENT DOCUMENTS

| WO | WO00/05201 | * | 2/2000 |
|----|------------|---|--------|
| WO | WO00/05223 | * | 2/2000 |
| WO | WO00/05224 | * | 2/2000 |
| WO | WO00/49005 | * | 8/2000 |
| WO | WO00/68213 | * | 11/2000 |

* cited by examiner

*Primary Examiner*—Ceila Chang
*Assistant Examiner*—Golam M M Shameem
(74) *Attorney, Agent, or Firm*—Ronald G. Ort

(57) ABSTRACT

The invention is directed to physiologically active compounds of general formula (I):

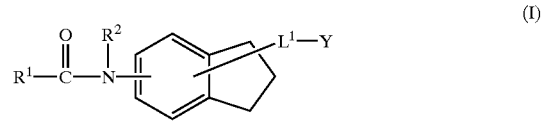

wherein:

$R^1$ represents aryl, heteroaryl or a group $R^3$—$L^2$—$Ar^1$—$L^3$—;

$R^2$ represents hydrogen or lower alkyl;

$R^3$ represents aryl or heteroaryl; and $Ar^1$ represents an optionally substituted saturated, partially saturated or fully unsaturated 8 to 10 membered bicyclic ring system containing at least one heteroatom selected from O, S or N;

Y is carboxy or an acid bioisostere;

and their corresponding N-oxides or prodrugs, and pharmaceutically acceptable salts and solvates of such compounds and their corresponding N-oxides or prodrugs.

Such compounds have valuable pharmaceutical properties, in particular the ability to regulate the interaction of VCAM-1 and fibronectin with the integrin VLA-4 (α4β1).

19 Claims, No Drawings

INDANE DERIVATIVES

CROSS-REFERENCE TO RELATED APPLICATIONS

This application is a continuation of PCT/GB01/00844, filed Feb. 28, 2001, which claims priority from GB Application No. 0004686.2, filed Feb. 28, 2000, both these applications incorporated herein by reference.

BACKGROUND OF THE INVENTION

This invention is directed to indane derivatives, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell-cell and cell-extracellular matrix interactions are mediated by protein ligands (e.g. fibronectin, VCAM-1 and vitronectin) and their integrin receptors [e.g. $\alpha 5\beta 1$ (VLA-5), $\alpha 4\beta 1$ (VLA-4) and $\alpha V\beta 3$]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called $\alpha$ and $\beta$. There are at least fifteen different $\alpha$-subunits ($\alpha 1-\alpha 9$, $\alpha$-L, $\alpha$-M, $\alpha$-X, $\alpha$-IIb, $\alpha$-V and $\alpha$-E) and at least seven different $\beta$ ($\beta 1-\beta 7$) subunits. The integrin family can be subdivided into classes based on the $\beta$ subunits, which can be associated with one or more $\alpha$-subunits. The most widely distributed integrins belong to the $\beta 1$ class, also known as the very late antigens (VLA). The second class of integrins are leukocyte specific receptors and consist of one of three $\alpha$-subunits $\alpha$-L, $\alpha$-M or $\alpha$-X) complexed with the $\beta 2$ protein. The cytoadhesins $\alpha$-IIb$\beta 3$ and $\alpha$-V$\beta 3$, constitute the third class of integrins.

The present invention principally relates to agents which modulate the interaction of the ligand VCAM-1 with its integrin receptor $\alpha 4\beta 1$ (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin $\alpha 4\beta 1$ mediates both cell-cell and cell-matrix interactions. Cells expressing $\alpha 4\beta 1$ bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by pro-inflammatory cytokines such as INF-$\gamma$, TNF-$\alpha$, IL-1$\beta$ and IL-4.

Regulation of $\alpha 4\beta 1$ mediated cell adhesion is important in numerous physiological processes, including T-cell proliferation, B-cell localisation to germinal centres, and adhesion of activated T-cells and eosinophils to endothelial cells. Evidence for the involvement of VLA-4VCAM-1 interaction in various disease processes such as melanoma cell division in metastasis, T-cell infiltration of synovial membranes in rheumatoid arthritis, autoimmune diabetes, colitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which $\alpha 4\beta 1$ binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J. Clin. Invest., 1994, 94, pages 655–662). In the oxazalone-sensitised model of inflammation (contact hypersensitivity response) in mice, intravenous administration of anti-$\alpha 4$ specific monoclonal antibodies significantly inhibited (50–60% reduction in the ear swelling response) the efferent response (P. L. Chisholm et al. J. Immunol., 1993, 23, pages 682–688). In a sheep model of allergic bronchoconstriction, HP½, an anti-$\alpha 4$ monoclonal antibody given intravenously or by aerosol, blocked the late response and the development of airway hyperresponsiveness (W. M. Abraham et al. J. Clin. Invest., 1994, 93 pages 776–787).

SUMMARY OF THE INVENTION

We have now found a novel group of indane derivatives which have valuable pharmaceutical properties, in particular the ability to regulate the interaction of VCAM-1 and fibronectin with the integrin VLA-4 ($\alpha 4\beta 1$).

Thus, in one aspect, the present invention is directed to compounds of general formula (I):

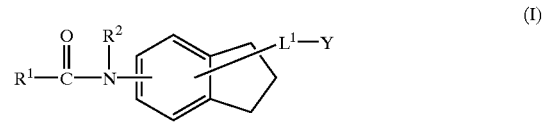

wherein:
$R^1$ represents aryl, heteroaryl or a group $R^3$—$L^2$—$Ar^1$—$L^3$—;
$R^2$ represents hydrogen or lower alkyl;
$R^3$ represents aryl or heteroaryl;
$R^4$ is alkyl, aryl, cycloalkyl, heteroaryl or heterocycloalkyl, or alkyl substituted by aryl, an acidic functional group, cycloalkyl, heteroaryl, heterocycloalkyl, —S(O)$_m$R$^5$, —C(=O)—NY$^3$Y$^4$ or —NY$^3$Y$^4$;
$R^5$ represents alkyl, alkenyl, alkynyl, aryl, arylalkyl, arylalkenyl, arylalkynyl, cycloalkyl, cycloalkylalkyl, cycloalkylalkenyl, cycloalkylalkynyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^6$ is hydrogen, alkyl, aryl, arylalkyl, cycloalkyl, cycloalkylalkyl, heteroaryl, heteroarylalkyl, heterocycloalkyl or heterocycloalkylalkyl;

$R^7$ is hydrogen, $R^5$ or alkyl substituted with alkoxy, cycloalkyl, hydroxy, mercapto, alkylthio or —$NY^3Y^4$;

$R^8$ is hydrogen or lower alkyl;

$R^9$ and $R^{11}$ are each independently selected from hydrogen or a group consisting of amino acid side chains, an acidic functional group, $R^5$, —C(=O)—$R^5$, or —C(=O)—$NY^3Y^4$, or alkyl substituted by an acidic functional group or by $R^5$, —$NY^3Y^4$, —NH—C(=O)—$R^5$, —C(=O)—$R^{12}$—$NH_2$, —C(=O)—$Ar^2$—$NH_2$, —C(=O)—$R^{12}$—$CO_2H$, or —C(=O)—$NY^3Y^4$;

or $R^7$ and $R^9$ together with the atoms to which they attached form a 3- to 6-membered heterocycloalkyl ring;

$R^{10}$ represents $C_{1-6}$alkylene, optionally substituted by $R^4$;

$R^{12}$ is an alkylene chain, an alkenylene chain, or an alkynylene chain;

$R^{13}$ is alkyl, aryl, arylalkyl, cycloalkyl, cycloalkylalkyl, heteroaryl, heteroarylalkyl, heterocycloalkyl or heterocycloalkylalkyl;

$Ar^1$ represents an optionally substituted saturated, partially saturated or fully unsaturated 8 to 10 membered bicyclic ring system containing at least one heteroatom selected from O, S or N;

$Ar^2$ is arylene or heteroaryldiyl;

$L^1$ represents
(i) a direct bond;
(ii) an alkenylene, alkylene or alkynylene linkage each optionally substituted by (a) an acidic functional group, cyano, oxo, —S(O)$_m R^4$, $R^5$, —C(=O)—$R^5$, —C(=O)—O$R^5$, —N($R^6$)—C(=Z)—$R^4$, —N($R^6$)—C(=O)—O$R^4$, —N($R^6$)—$SO_2$—$R^4$, —$NY^3Y^4$ or —[C(=O)—N($R^7$)—C($R^8$)($R^9$)]$_p$—C(=O)—$NY^3Y^4$, or by (b) alkyl substituted by an acidic functional group, or by S(O)$_m R^4$, —C(=Z)—$NY^3Y^4$ or —$NY^3Y^4$;
(iii) a —[C(=O)—N($R^7$)—C($R^8$)($R^9$)]$_p$— linkage;
(iv) a —$Z^1$—$R^{10}$— linkage;
(v) a —$R^{10}$—$Z^1$—$R^{10}$— linkage;
(vi) a —C($R^8$)($R^{11}$)—[C(=O)—N($R^7$)—C($R^8$)($R^9$)]$_p$— linkage; or
(vii) a —$L^4$—$L^5$—$L^6$— linkage;

$L^2$ represents $NR^8$;

$L^3$ represents an alkylene, alkenylene or alkynylene chain;

$L^4$ and $L^6$ each independently represent a direct bond or an alkylene chain;

$L^5$ represents a cycloalkylene or an indanylene;

Y is carboxy or an acid bioisostere;

$Y^1$ and $Y^2$ are independently hydrogen, alkenyl, alkyl, aryl, arylalkyl, cycloalkyl, heteroaryl or heteroarylalkyl; or the group —$NY^1Y^2$ may form a cyclic amine;

$Y^3$ and $Y^4$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^1Y^2$, or one or more —$CO_2R^6$ or —C(=O)—$NY^1Y^2$ groups; or the group —$NY^3Y^4$ may form a 5- to 7-membered cyclic amine which (i) may be optionally substituted with one or more substituents selected from alkoxy, carboxamido, carboxy, hydroxy, oxo (or a 5-, 6- or 7-membered cyclic acetal derivative thereof), $R^7$; (ii) may also contain a further heteroatom selected from O, S, $SO_2$, or $NY^5$; and (iii) may also be fused to additional aryl, heteroaryl, heterocycloalkyl or cycloalkyl rings to form a bicyclic or tricyclic ring system;

$Y^5$ is hydrogen, alkyl, aryl, arylalkyl, —C(=O)—$R^{13}$, —C(=O)—O$R^{13}$ or —$SO_2R^{13}$;

Z is O or S;

$Z^1$ is O, S(O)$_m$, $NR^8$, $SO_2NR^8$, C(=O)$NR^8$ or C(=O);

m is an integer 1 or 2;

n is zero or an integer 1 or 2;

p is zero or an integer 1 to 4;

the group

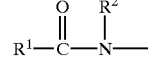

is attached to the benzene ring of the indane system and the group —$L^1$—Y is attached to either ring of the indane system; and any aryl or heteroaryl moieties present as a group or part of a group may be optionally substituted; but excluding compounds where an oxygen, nitrogen or sulfur atom is attached directly to a carbon carbon multiple bond of an alkenylene, alkynylene or cycloalkenylene residue; and the corresponding N-oxides, and their prodrugs; and pharmaceutically acceptable salts and solvates (e.g. hydrates) of such compounds and their N-oxides and prodrugs.

DETAILED DESCRIPTION

In the present specification, the term "compounds of the invention", and equivalent expressions, are meant to embrace compounds of general formula (I) as hereinbefore described, which expression includes the prodrugs, protected derivatives of compounds of formula (I) containing one or more acidic functional groups and/or amino-acid side chains, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986, 21, page 283 "Bioisosterism In Drug Design"; Yun, Hwahak Sekye, 1993, 33, pages 576–579 "Application Of Bioisosterism To New Drug Design"; Zhao, Huaxue Tongbao, 1995, pages 34–38 "Bioisosteric Replacement And Development Of Lead Compounds In Drug Design"; Graham, Theochem, 1995, 343, pages 105–109 "Theoretical Studies Applied To Drug Design:ab initio Electronic Distributions In Bioisosteres"). Examples of suitable acid bioisosteres include: —C(=O)—NHOH, —C(=O)—$CH_2OH$, —C(=O)—$CH_2SH$, —C(=O)—NH—CN, sulfo, phosphono, alkylsulfonylcarbamoyl, tetrazolyl, arylsulfonylcarbamoyl, heteroarylsulfonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-l-methylpyrazolyl.

"Acidic functional group" means a group with an acidic hydrogen within it. The "protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups (i.e. —$CO_2R^{13}$), ethers of hydroxy groups (i.e. —$OR^{13}$), thioethers of mercapto groups (i.e. —$SR^{13}$), and N-benzyl derivatives of imidazoles.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. "Branched", as used herein and throughout the text, means that one or more lower alkyl groups such as methyl, ethyl or propyl are attached to a linear chain; here a linear alkenyl chain.

"Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulfinyl or lower alkylsulfonyl group means unless otherwise specified, an aliphatic hydrocarbon group which may be straight or branched having about 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkyl-O— group in which the alkyl group is as defined above. Exemplary alkylenedioxy groups include methylenedioxy and ethylenedioxy.

"Alkylsulfinyl" means an alkyl-SO— group in which the alkyl group is as previously described. Preferred alkylsulfinyl groups are those in which the alkyl group is $C_{1-4}$alkyl.

"Alkylsulfonyl" means an alkyl-$SO_2$— group in which the alkyl group is as previously described. Preferred alkylsulfonyl groups are those in which the alkyl group is $C_{1-4}$alkyl.

"Alkylsulfonylcarbamoyl" means an alkyl-$SO_2$—NH—C(=O)— group in which the alkyl group is as previously described. Preferred alkylsulfonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a $C_{2-6}$alkynyl group. Exemplary alkynylene radicals include ethynylene and propynylene.

"Amino acid side chains" means the substituent found on the carbon between the amino and carboxy groups in α-amino acids. For examples of "protected derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyloxy, heteroaroylamino, heteroaryloxy, hydroxy, nitro, trifluoromethyl, —$NY^1Y^2$, —$CONY^1Y^2$, —$SO_2NY^1Y^2$, —$Z^2$—$C_{2-6}$alkylene-$NY^1Y^2$ {where $Z^2$ is O, $NR^8$ or $S(O)_n$}, —$NY^1$—(C=O)alkyl, —$NY^1$-$SO_2$alkyl or alkyl optionally substituted with aryl, heteroaryl, hydroxy, or —$NY^1Y^2$.

"Arylalkenyl" means an aryl-alkenyl-group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl-group in which the aryl and alkynyl are as previously described. Exemplary arylalkynyl groups include phenylethynyl and 3-phenylbut-2-ynyl.

"Arylene" means an optionally substituted bivalent radical derived from an aryl group. Exemplary arylene groups include optionally substituted phenylene, naphthylene and indanylene.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulfinyl" means an aryl-SO— group in which the aryl group is as previously described.

"Arylsulfonyl" means an aryl-$SO_2$— group in which the aryl group is as previously described.

"Arylsulfonylcarbamoyl" means an aryl-$SO_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryl" means an aromatic carbocyclic moiety of about 5 to about 10 ring members in which one of the ring members is nitrogen and the other ring members are chosen from carbon, oxygen, sulfur, or nitrogen. Examples of azaheteroaryl groups include benzimidazolyl, imidazolyl, isoquinolinyl, isoxazolyl, pyrazolopyrimidinyl, pyridyl, pyrimidinyl, quinolinyl, quinazolinyl and thiazolyl.

"Azaheteroaryldiyl" means an optionally substituted bivalent radical derived from a heteroaryl group.

"Cyclic amine" means a 3 to 8 membered monocyclic cycloalkyl ring system where one of the ring carbon atoms is replaced by nitrogen and which (i) may optionally contain an additional heteroatom selected from O, S or $NY^6$ (where $Y^6$ is hydrogen, alkyl, arylalkyl, and aryl) and (ii) may be fused to additional aryl or heteroaryl ring to form a bicyclic ring system. Exemplary cyclic amines include pyrrolidine, piperidine, morpholine, piperazine, indoline and pyrindoline.

"Cycloalkenyl" means a non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl-group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from an unsaturated monocyclic hydrocarbon of about 3 to about 10 carbon atoms by removing a hydrogen atom from each of two different carbon atoms of the ring. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include $C_{3-8}$cycloalkyl rings such as cyclopropyl, cyclopentyl, cyclohexyl and cycloheptyl.

"Cycloalkylalkenyl" means a cycloalkyl-alkenyl-group in which the cycloalkyl and alkenyl moieties are as previously described. Exemplary monocyclic cycloalkylalkenyl groups include cyclopentylvinylene and cyclohexylvinylene.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylalkynyl" means a cycloalkyl-alkynyl-group in which the cycloalkyl and alkynyl moieties are as previously described. Exemplary monocyclic cycloalkylalkynyl groups include cyclopropylethynyl, cyclopentylethynyl and cyclohexylethynyl.

"Cycloalkylene" means a bivalent radical derived from a saturated monocyclic hydrocarbon of about 3 to about 10 carbon atoms by removing a hydrogen atom from each of two different carbon atoms of the ring. Exemplary cycloalkenylene radicals include cyclopropylene, cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulfur (examples of such groups include benzimidazolyl, benzthiazolyl, furyl, imidazolyl, indolyl, indolizinyl, isoxazolyl, isoquinolinyl, isothiazolyl, oxadiazolyl, oxazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above. When $R^1$ is an optionally substituted heteroaryl group this may particularly represent an optionally substituted "azaheteroaryl" group.

"Heteroarylalkenyl" means a heteroaryl-alkenyl-group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl-group in which the heteroaryl and alkyl moieties are as previously described. Preferred heteroarylalkyl groups contain a $C_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl-group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from an aromatic monocyclic or multicyclic organic moiety of about 5 to about 10 ring members in which one or more of the ring members is/are element(s) other than carbon, for example nitrogen, oxygen or sulfur, and optionally substituted by one or more "aryl group substituents" as defined above.

"Heteroaryloxy" means an heteroaryl-O— group in which the heteroaryl group is as previously described. Exemplary heteroaryloxy groups include optionally substituted pyridyloxy.

"Heteroarylsulfonylcarbamoyl" means a heteroaryl-$SO_2$—NH—C(=O)— group in which the heteroaryl group is as previously described.

"Heterocycloalkyl" means: (i) a cycloalkyl group of about 3 to 7 ring members which contains one or more heteroatoms selected from O, S or $NY^3$ and which may optionally be substituted by oxo; (ii) an optionally substituted partially saturated multicyclic heterocarbocyclic moiety in which an aryl (or heteroaryl ring) and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a saturated monocyclic hydrocarbon of about 5 to about 7 atoms, which contains one or more heteroatoms selected from O, S or $NY^6$ and is optionally substituted by oxo, by removing a hydrogen atom from each of two different carbon atoms of the ring, or when $NY^6$ is NH by removing a hydrogen atom from one carbon atom of the ring and a hydrogen atom from the NH, or when the ring contains two $NY^6$ heteroatoms and $NY^6$ is NH by removing a hydrogen atom from both nitrogen atoms.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

Suitable esters of compounds of formula (I) containing a carboxy group, are for example those described by F. J. Leinweber, Drug Metab. Res., 1987, 18, page 379.

Suitable esters of compounds of formula (I) containing both a carboxy group and a hydroxy group within the moiety —$L^1$—Y, include lactones, formed by loss of water between said carboxy and hydroxy groups. Examples of lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent optionally substituted aryl, such as optionally substituted phenyl [preferred optional substituents include one or more groups (e.g. 1 or 2) selected from aryloxy, cyano, halo (e.g. chloro or fluoro), lower alkoxy (e.g. methoxy), lower alkyl (e.g. methyl), nitro and perfluoroloweralkyl (e.g. trifluoromethyl)]. $R^1$ especially represents substituted phenyl selected from 2-chlorophenyl, 5-chloro-2-cyanophenyl, 2-chloro-6-methylphenyl, 2,6-dichlorophenyl, 2,6-difluoropheny,4-fluoro-2-trifluoromethyl, 2-methyl-4-nitrophenyl, 2-methyl-5-nitrophenyl, 2-nitrophenyl, 3-nitrophenyl or 2-phenoxyphenyl.

$R^1$ may also particularly represent optionally substituted heteroaryl, such as benzoxazole, benzimidazole, isoquinolinyl, isoxazolyl, pyrazolopyrimidinyl, pyridyl, pyrimidinyl, quinolinyl, thiazolyl and triazolyl, each optionally substituted by one or more (e.g. 1 or 2) aryl group substituents as described hereinbefore [preferred optional substituents include alkyl-C(=O)—, aryl, cyano, halo, (e.g. chloro or fluoro), lower alkoxy (e.g. methoxy), lower alkyl (e.g. methyl), lower alkylsulfonyl, lower alkylthio, nitro and perfluoroloweralkyl (e.g. trifluoromethyl) and —$NY^1Y^2$]. $R^1$ especially represents an optionally substituted azaheteroaryl selected from quinolin-4-yl, isoquinolin-2-yl, 2,4-pyridin-3-yl, 2,6-dimethyl-4-trifluoromethylpyridin-3-yl, 4-trifluoromethylpyridin-3-yl, 2-phenyl-4-methyl-1,2,3-triazol-5-yl, 3,5-dimethylisoxazol-4-yl, 2,7-dimethylpyrazolo-[1,5-a]pyrimidin-6-yl, 2-isopropyl-4-methylthiazol-5-yl and 4-trifluoromethylpyrimidin-5-yl.

$R^1$ may also particularly represent a group $R^3$—$L^2$—$Ar^1$—$L^3$- in which: $R^3$ and $L^2$ are as define above; $L^3$ represents a straight or branched $C_{1-6}$alkylene chain, more particularly a straight $C_{1-4}$alkylene chain such as methylene or ethylene, preferably methylene and $Ar^1$ is an 8 to 10 membered bicyclic system

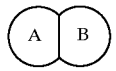

in which ring

is a 5 or 6 membered, preferably a 5 membered, heteroaryl ring and ring

is a 5 or 6 membered heteroaryl ring or a benzene ring, preferably a benzene ring, each ring optionally substituted by one or more (e.g. 1 or 2) "aryl group substituents" as defined above and the two rings are joined together by a carbon-carbon linkage or a carbon-nitrogen linkage.

is preferably benzoxazolyl or benzimidazolyl, in which ring

is optionally substituted by one or more (e.g. 1 or 2) "aryl group substituents" as defined above [examples of particular aryl group substituents include $C_{1-4}$alkyl (e.g. methyl or ethyl), $C_{1-4}$alkoxy (e.g. methoxy), amino, halogen, hydroxy, $C_{1-4}$alkylthio, $C_{1-4}$alkylsulfinyl, $C_{1-4}$alkylsulfonyl, nitro or trifluoromethyl]. Within $R^3$—$L^2$—$Ar^1$—$L^3$—, $L^2$ is preferably NH and $R^3$ is particularly optionally substituted aryl, such as monosubstituted or disubstituted phenyl, [examples of particular aryl group substituents include lower alkyl (e.g. methyl), lower alkoxy (e.g. methoxy), halo (e.g. fluoro or chloro) and $Y^1Y^2N$— (e.g. dimethylamino)].

$R^2$ may particularly represent hydrogen.

$R^2$ may also particularly represent lower alkyl, (e.g. methyl).

$L^1$ may particularly represent an optionally substituted alkylene linkage (e.g. optionally substituted methylene, optionally substituted ethylene or optionally substituted propylene). Preferred optional substituents include lower alkyl, aryl, heteroaryl, —ZH, —$ZR^{13}$, —N($R^6$)—C(=O)—$R^4$, —N($R^6$)—C(=O)—$OR^4$, —N($R^6$)—$SO_2$—$R^4$, —$NY^3Y^4$ and —[C(=O)—N($R^7$)—C($R^8$)($R^9$)]$_p$—C(=O)—$NY^3Y^4$ or alkyl substituted by carboxy (or an acid bioisostere), —ZH, —$ZR^{13}$, —C(=O)—$NY^3Y^4$ or —$NY^3Y^4$. In one preferred embodiment $L^1$ is methylene. In another preferred embodiment $L^1$ is a group

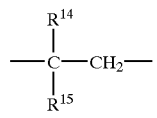

[where $R^{14}$ is hydrogen or lower alkyl (e.g. methyl) and $R^{15}$ represents hydrogen or lower alkyl, or where $R^{14}$ is hydrogen and $R^{15}$ represents aryl, heteroaryl, —N($R^6$)—C(=O)—$R^4$, —N($R^6$)—C(=O)—$OR^4$, —N($R^6$)—$SO_2$—$R^4$, —$NY^3Y^4$ or —[C(=O)—N($R^7$)—C($R^8$)($R^9$)]$_p$—C(=)—$NY^3Y^4$, or alkyl substituted by carboxy (or an acid bioisostere), —ZH, —ZR$^{13}$, —C(=O)—NY$^3$Y$^4$ or —NY$^3$Y$^4$], and is more preferably a group

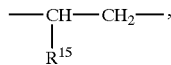

particularly

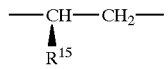

[where R$^{15}$ represents hydrogen, lower alkyl, aryl, heteroaryl, —N(R$^6$)—C(=O)—R$^4$, —N(R$^6$)—C(=O)—OR$^4$, —N(R$^6$)—SO$_2$—R$^4$ or —NY$^3$Y$^4$ or alkyl substituted by carboxy, —OH, —OR$^{13}$ or —C(=O)—NY$^3$Y$^4$]. In another preferred embodiment L$^1$ is a group

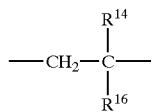

[where R$^{14}$ is hydrogen or lower alkyl (e.g. methyl) and R$^{16}$ represents lower alkyl, or where R$^{14}$ is hydrogen and R$^{16}$ represents aryl, heteroaryl, —N(R$^6$)—C(=O)—R$^4$, —N(R$^6$)—C(=O)—OR$^4$, —N(R$^6$)—SO$_2$—R$^4$, —NY$^3$Y$^4$ or —[C(=O)—N(R$^7$)—C(R$^8$(R$^9$)]$_p$—C(=O)—NY$^3$Y$^4$, or alkyl substituted by carboxy (or an acid bioisostere), —ZH, —ZR$^{13}$, —C(=O)—NY$^3$Y$^4$ or —NY$^3$Y$^4$], and is more preferably a group

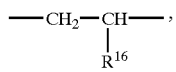

particularly

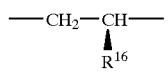

[where R$^{16}$ represents —N(R$^6$)—C(=O)—R$^4$, or —N(R$^6$)—SO$_2$—R$^4$].

L$^1$ may also particularly represent a —L$^4$—L$^5$—L$^6$— linkage, in which L$^4$ and L$^6$ are independently a direct bond or alkylene (e.g. methylene) and L$^5$ is cycloalkylene, such as cyclopropylene or cyclopentylene, or indanylene.

Y may particularly represent carboxy.

It is to be understood that this invention covers all appropriate combinations of the particular and preferred groupings referred to herein.

A particular group of compounds of the invention are compounds of formula (Ia):

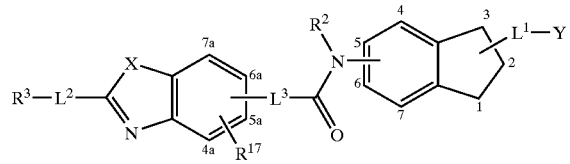

in which R$^2$, R$^3$, L$^1$, L$^2$, L$^3$ and Y are as hereinbefore defined; X is O or NR$^{18}$ (where R$^{18}$ is hydrogen or lower alkyl); and R$^{17}$ is hydrogen, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyloxy, heteroaroylamino, heteroaryloxy, hydroxy, nitro, trifluoromethyl, —NY$^1$Y$^2$, —CONY$^1$Y$^2$, —SO$_2$NY$^1$Y$^2$, —Z$^2$—C$_{2-6}$alklene-NY$^1$Y$^2$, —NY$^1$—(C=O)alkyl, —NY$^1$—SO$_2$alkyl or alkyl optionally substituted with aryl, heteroaryl, hydroxy, or —NY$^1$Y$^2$ (where Y$^1$, Y$^2$ and Z$^2$ are as defined hereinbefore), and the corresponding N-oxides, and their prodrugs; and pharmaceutically acceptable salts and solvates (e.g. hydrates) of such compounds and their N-oxides and prodrugs.

Compounds of formula (Ia) in which R$^3$ represents optionally substituted aryl, especially monosubstituted or disubstituted phenyl, are preferred. Preferred optional substituents include lower alkyl (e.g. methyl), lower alkoxy (e.g. methoxy), halo (e.g. fluoro or chloro) and Y$^1$Y$^2$N— (e.g. dimethylamino). R$^3$ especially represents phenyl substituted in at least the 2-position, for example by a C$_{1-4}$alkyl group such as methyl.

Compounds of formula (Ia) in which L$^2$ represents NH are preferred.

Compounds of formula (Ia) in which R$^{17}$ represents hydrogen, halo (e.g. chloro), lower alkyl (e.g. methyl or ethyl) or lower alkoxy (e.g. methoxy) are preferred.

Compounds of formula (Ia) in which L$^3$ represents a straight or branched C$_{1-6}$alkylene chain, especially a straight C$_{1-4}$alkylene chain, more especially methylene, are preferred.

Compounds of formula (Ia) in which R$^2$ represents hydrogen are preferred.

Compounds of formula (Ia) in which R$^2$ represents lower alkyl, (e.g. methyl) are also preferred.

Compounds of formula (Ia) in which L$^1$ represents an optionally substituted alkylene linkage (e.g. optionally substituted methylene, optionally substituted ethylene or optionally substituted propylene) are preferred. Preferred optional substituents include lower alkyl, aryl, heteroaryl, —ZH, —ZR$^{13}$, —N(R$^6$)—C(=O)—R$^4$, —N(R$^6$)—C(=O)—OR$^4$, —N(R$^6$)—SO$_2$—R$^4$, —NY$^3$Y$^4$ and —[C(=O)—N(R$^7$)—C(R$^8$)(R$^9$)]$_p$—C(=O)—NY$^3$Y$^4$ or alkyl substituted by carboxy (or anacid bioisostere), —ZH —ZR$^{13}$, —C(=O)—NY$^3$Y$^4$ or —NY$^3$Y$^4$. In one preferred embodiment L$^1$ is methylene. In another preferred embodiment L$^1$ is a group

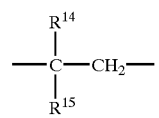

[where R$^{14}$ is hydrogen or lower alkyl (e.g. methyl) and R$^{15}$ represents hydrogen or lower alkyl, or where R$^{14}$ is hydrogen and R$^{15}$ represents aryl, heteroaryl, —N(R$^6$)—C(=O)—R$^4$, —N(R$^6$)—C(=O)—OR$^4$, —N(R$^6$)—SO$_2$—R$^4$, —NY$^3$T$^4$ or —[C(=O)—N(R$^7$)—C(R$^8$)(R$^9$)]$_p$—C(=O)—NY$^3$Y$^4$, or alkyl substituted by carboxy (or an acid bioisostere), —ZH, —ZR$^{13}$, —C(=O)—NY$^3$Y$^4$ or —NY$^3$Y$^4$], and is more preferably a group

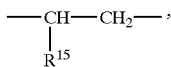

particularly

[where $R^{15}$ represents hydrogen, lower alkyl, aryl, heteroaryl, —N($R^6$)—C(=O)—$R^4$, —N($R^6$)—C(=O)—O$R^4$, —N($R^6$)—SO$_2$—$R^4$ or —N$Y^3Y^4$ or alkyl substituted by carboxy, —OH, —O$R^{13}$ or —C(=O)—N$Y^3Y^4$]. In another preferred embodiment $L^1$ is a group

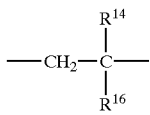

[where $R^{14}$ is hydrogen or lower alkyl (e.g. methyl) and $R^{16}$ represents lower alkyl, or where $R^{14}$ is hydrogen and $R^{16}$ represents aryl, heteroaryl, —N($R^6$)—C(=O)—$R^4$, —N($R^6$)—C(=O)—O$R^4$, —N($R^6$)—SO$_2$—$R^4$, —N$Y^3Y^4$ or —[C(=O)—N($R^7$)—C($R^8$)($R^9$)]$_p$—C(=O)—N$Y^3Y^4$, or alkyl substituted by carboxy (or an acid bioisostere), —ZH, —Z$R^{13}$, —C(=O)—N$Y^3Y^4$ or —N$Y^3Y^4$], and is more preferably a group

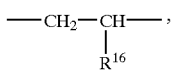

particularly

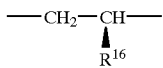

[where $R^{16}$ represents —N($R^6$)—C(=O)—$R^4$, or —N($R^6$)—SO$_2$—$R^4$].

Compounds of formula (Ia) in which $L^1$ represents a —$L^4$—$L^5$—$L^6$— linkage, in which $L^4$ and $L^6$ are independently a direct bond or alkylene (e.g. methylene) and $L^5$ is cycloalkylene, such as cyclopropylene or cyclopentylene, or indanylene are also preferred.

Compounds of formula (Ia) in which Y represents carboxy are preferred.

A preferred group of compounds of the invention are compounds of formula (Ia) in which: $R^2$ is hydrogen or lower alkyl (e.g. methyl); $R^3$ is optionally substituted phenyl (especially phenyl substituted in at least the 2-position, e.g. by $C_{14}$alkyl); $R^{17}$ is hydrogen, chloro, $C_{1-4}$alkyl, or $C_{1-4}$alkoxy; $L^1$ is methylene; $L^2$ is NH; $L^3$ is a straight $C_{1-4}$alkylene chain, especially methylene; X is O; Y is carboxy; the group

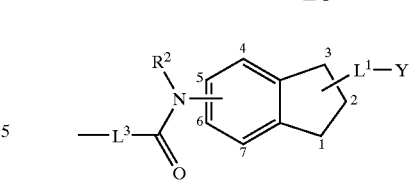

is attached at the benzoxazole ring 6a position; the nitrogen atom of the

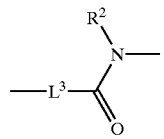

linkage is attached to the indane ring 5 or 6 position; and the —$L^1$—Y group is attached to the indane ring 1 or 2 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ia) in which: $R^2$ is hydrogen or lower alkyl (e.g. methyl); $R^3$ is optionally substituted phenyl (especially phenyl substituted in at least the 2-position, e.g. by $C_{1-4}$alkyl); $R^{17}$ is hydrogen, chloro, $C_{1-4}$alkyl, or $C_{1-4}$alkoxy; $L^1$ is methylene; $L^2$ is NH; $L^3$ is a straight $C_{1-4}$alkylene chain, especially methylene; X is N$R^{18}$ (especially NH); Y is carboxy; the group

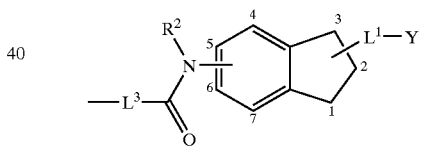

is attached at the benzimidazole ring 5a or 6a position; the nitrogen atom of the

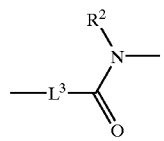

linkage is attached to the indane ring 5 or 6 position; and the —$L^1$—Y group is attached to the indane ring 1 or 2 position; and the corresponding N-oxides, and their prodrugs; and pharmaceutically acceptable salts and solvates (e.g. hydrates) of such compounds and their N-oxides and prodrugs.

Another particular group of compounds of the invention are compounds of formula (Ib):

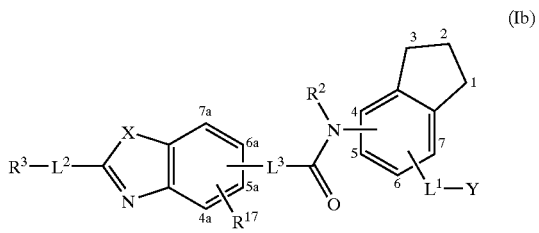

in which $R^2$, $R^3$, $L^1$, $L^2$, $L^3$ and Y are as hereinbefore defined; X is O or $NR^{18}$ (where $R^{18}$ is hydrogen or lower alkyl); and $R^{17}$ is hydrogen, acyl, acylamino, alkoxy, alkoxycarbonyl, alkylenedioxy, alkylsulfinyl, alkylsulfonyl, alkylthio, aroyl, aroylamino, aryl, arylalkyloxy, arylalkyloxycarbonyl, arylalkylthio, aryloxy, aryloxycarbonyl, arylsulfinyl, arylsulfonyl, arylthio, carboxy, cyano, halo, heteroaroyl, heteroaryl, heteroarylalkyloxy, heteroaroylamino, heteroaryloxy, hydroxy, nitro, trifluoromethyl, $-NY^1Y^2$, $-CONY^1Y^2$, $-SO_2NY^1Y^2$, $-Z^2-C_{2-6}$alkylene-$NY^1Y^2$, $-NY^1-(C=O)$alkyl, $-NY^1-SO_2$alkyl or alkyl optionally substituted with aryl, heteroaryl, hydroxy, or $-NY^1Y^2$ (where $Y^1$, $Y^2$ and $Z^2$ are as defined hereinbefore), and the corresponding N-oxides, and their prodrugs; and pharmaceutically acceptable salts and solvates (e.g. hydrates) of such compounds and their N-oxides and prodrugs.

Compounds of formula (Ib) in which $R^3$ represents optionally substituted aryl, especially monosubstituted or disubstituted phenyl, are preferred. Preferred optional substituents include lower alkyl (e.g. methyl), lower alkoxy (e.g. methoxy), halo (e.g. fluoro or chloro) and $Y^1Y^2N-$ (e.g. dimethylamino). $R^3$ especially represents phenyl substituted in at least the 2-position, for example by a $C_{1-4}$alkyl group such as methyl.

Compounds of formula (Ib) in which $L^2$ represents NH are preferred.

Compounds of formula (Ib) in which $R^{17}$ represents hydrogen, halo (e.g. chloro), lower alkyl (e.g. methyl or ethyl) or lower alkoxy (e.g. methoxy) are preferred.

Compounds of formula (Ib) in which $L^3$ represents a straight or branched $C_{1-6}$alkylene chain, especially a straight $C_{1-4}$alkylene chain, more especially methylene, are preferred.

Compounds of formula (Ib) in which $R^2$ represents hydrogen are preferred.

Compounds of formula (Ib) in which $R^2$ represents lower alkyl, (e.g. methyl) are also preferred.

Compounds of formula (Ib) in which $L^1$ represents an optionally substituted alkylene linkage (e.g. optionally substituted methylene, optionally substituted ethylene or optionally substituted propylene) are preferred. Preferred optional substituents include lower alkyl, aryl, heteroaryl, $-ZH$, $-ZR^{13}$, $-N(R^6)-C(=O)-R^4$, $-N(R^6)-C(=O)-OR^4$, $-N(R^6)-SO_2-R^4$, $-NY^3Y^4$ and $-[C(=O)-N(R^7)-C(R^8)(R^9)]_p-C(=O)-NY^3Y^4$ or alkyl substituted by carboxy (or an acid bioisostere), $-ZH$, $-ZR^{13}$, $-C(=O)-NY^3Y^4$ or $-NY^3Y^4$. In one preferred embodiment $L^1$ is a group

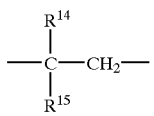

[where $R^{14}$ is hydrogen or lower alkyl (e.g. methyl) and $R^{15}$ represents hydrogen or lower alkyl, or where $R^{14}$ is hydrogen and $R^{15}$ represents aryl, heteroaryl, $-N(R^6)-C(=O)-R^4$, $-N(R^6)-C(=O)-OR^4$, $-N(R^6)-SO_2-R^4$, $-NY^3Y^4$ or $-[C(=O)-N(R^7)-C(R^8)(R^9)]_p-C(=O)-NY^3Y^4$, or alkyl substituted by carboxy (or an acid bioisostere), $-ZH$, $-ZR^{13}$, $-C(=O)-NY^3Y^4$ or $-NY^3Y^4$], and is more preferably a group

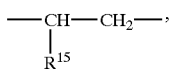

particularly

[where $R^{15}$ represents hydrogen, lower alkyl, aryl, heteroaryl, $-N(R^6)-C(=O)-R^4$, $-N(R^6)-C(=O)-OR^4$, $-N(R^6)-SO_2-R^4$ or $-NY^3Y^4$ or alkyl substituted by carboxy, $-OH$, $-OR^{13}$ or $-C(=O)-NY^3Y^4$]. In another preferred embodiment $L^1$ is a group

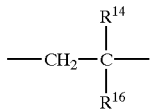

[where $R^{14}$ is hydrogen or lower alkyl (e.g. methyl) and $R^{16}$ represents lower alkyl, or where $R^{14}$ is hydrogen and $R^{16}$ represents aryl, heteroaryl, $-N(R^6)-C(=O)-R^4$, $-N(R^6)-C(=O)-OR^4$, $-N(R^6)-SO_2-R^4$, $-NY^3Y^4$ or $-[C(=O)-N(R^7)-C(R^8)(R^9)]_p-C(=O)-NY^3Y^4$, or alkyl substituted by carboxy (or an an acid bioisostere), $-ZH$, $-ZR^{13}$, $-C(=O)-NY^3Y^4$ or $-NY^3Y^4$], and is more preferably a group

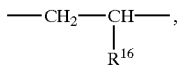

particularly

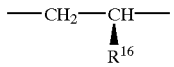

[where $R^{16}$ represents $-N(R^6)-C(=O)-R^4$, or $-N(R^6)-SO_2-R^4$].

Compounds of formula (Ib) in which $L^1$ represents a $-L^4-L^5-L^6-$ linkage, in which $L^4$ and $L^6$ are independently a direct bond or alkylene (e.g. methylene) and $L^5$ is cycloalkylene, such as cyclopropylene or cyclopentylene, or indanylene are also preferred.

Compounds of formula (Ib) in which Y represents carboxy are preferred.

A preferred group of compounds of the invention are compounds of formula (Ib) in which: $R^2$ is hydrogen or lower alkyl (e.g. methyl); R³ is optionally substituted phenyl (especially phenyl substituted in at least the 2-position, e.g. by $C_{1-4}$alkyl); $R^{17}$ is hydrogen, chloro, $C_{1-4}$alkyl, or $C_{1-4}$alkoxy; $L^1$ is a

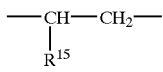

group particularly a

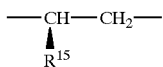

group, where $R^{15}$ represents hydrogen, lower alkyl, aryl, heteroaryl, —N(R⁶)—C(=O)—R⁴, —N(R⁶)—C(=O)—OR⁴, —N(R⁶)—SO₂—R⁴ or —NY³Y⁴, or alkyl substituted by carboxy (or an acid bioisostere), —OH, —OR¹³, —C(=O)—NY³Y⁴ or —NY³Y⁴; $L^2$ is NH; $L^3$ is a straight or branched $C_{1-4}$alkylene chain, especially methylene; X is O; Y is carboxy; the group

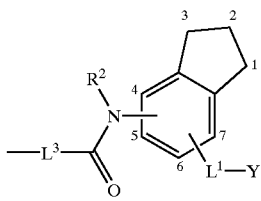

is attached at the benzoxazole ring 6a position; the nitrogen atom of the

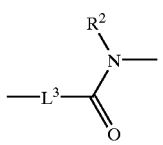

linkage is attached to the indane ring 4 position; and the —$L^1$—Y group is attached to the indane ring 7 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: R² is hydrogen or lower alkyl (e.g. methyl); R³ is optionally substituted phenyl (especially phenyl substituted in at least the 2-position, e.g. by $C_{1-4}$alkyl); $R^{17}$ is hydrogen, chloro, $C_{1-4}$alkyl, or $C_{1-4}$alkoxy; $L^1$ is a

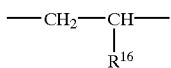

group, particularly

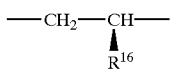

[where $R^{16}$ represents —N(R⁶)—C(=O)—R⁴, or —N(R⁶)—SO₂—R⁴]; $L^2$ is NH; $L^3$ is a straight $C_{1-4}$alkylene chain, especially methylene; X is O; Y is carboxy; the group

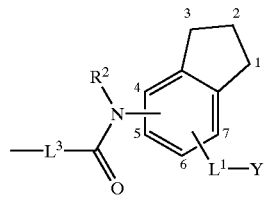

is attached at the benzoxazole ring 6a position; the nitrogen atom of the

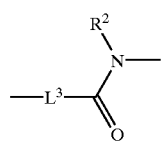

linkage is attached to the indane ring 4 position; and the —$L^1$—Y group is attached to the indane ring 7 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: R² is hydrogen or lower alkyl (e.g. methyl); R³ is optionally substituted phenyl (especially phenyl substituted in at least the 2-position, e.g. by $C_{1-4}$alkyl); $R^{17}$ is hydrogen, chloro, $C_{1-4}$alkyl, or $C_{1-4}$alkoxy; $L^1$ is a

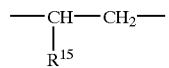

group particularly a

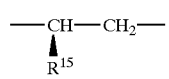

group, where $R^{15}$ represents hydrogen, lower alkyl, aryl, heteroaryl, —N(R⁶)—C(=O)—R⁴, —N(R⁶)—C(—O)—OR⁴, —N(R⁶)—SO₂—$_R$⁴ or —NY³Y⁴, or alkyl substituted by carboxy (or an acid bioisostere), —OH, —OR¹³, —C(=O)—NY³Y⁴ or —NY³Y⁴;]; $L^2$ is NH; $L^3$ is a straight $C_{1-4}$alkylene chain, especially methylene; X is $NR^{18}$ (especially NH); Y is carboxy; the group

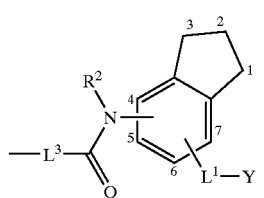

is attached at the benzimidazole ring 5a or 6a position; the nitrogen atom of the

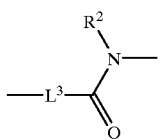

linkage is attached to the indane ring 4 position; and the —L¹—Y group is attached to the indane ring 7 position; and the corresponding N-oxides, and their prodrugs; and pharmaceutically acceptable salts and solvates (e.g. hydrates) of such compounds and their N-oxides and prodrugs.

Another preferred group of compounds of the invention are compounds of formula (Ib) in which: $R^2$ is hydrogen or lower alkyl (e.g. methyl); $R^3$ is optionally substituted phenyl (especially phenyl substituted in at least the 2-position, e.g. by $C_{1-4}$alkyl); $R^{17}$ is hydrogen, chloro, $C_{1-4}$alkyl, or $C_{1-4}$alkoxy; $L^1$ is a

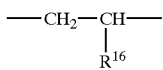

group, particularly

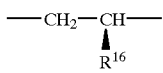

[where $R^{16}$ represents —N($R^6$)—C(=O)—$R^4$, or —N($R^6$)—SO₂—$R^4$]; $L^2$ is NH; $L^3$ is a straight $C_{1-4}$alkylene chain, especially methylene; X is $NR^{18}$ (especially NH); Y is carboxy; the group

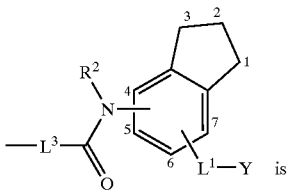

is attached at the benzimidazole ring 5a or 6a position; the nitrogen atom of the

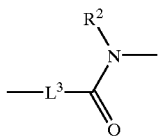

linkage is attached to the indane ring 4 position; and the —L¹—Y group is attached to the indane ring 7 position; and the corresponding N-oxides, and their prodrugs; and pharmaceutically acceptable salts and solvates (e.g. hydrates) of such compounds and their N-oxides and prodrugs.

Particular compounds of the invention of formula I(a) are selected from the compounds formed by joining the carbon atom (C*) of one of the fragments (A1 to A36) shown in Table 1 to the nitrogen atom (N*) of one of the fragments (B5 to B12) shown in Table 2, and joining the carbon atom (C*) of one of the fragments (B5 to B12) shown in Table 2 to the carbon atom (C*) of one of the acidic fragments (C1 to C3) depicted in Table 3.

Particular compounds of the invention of formula I(b) are selected from the compounds formed by joining the carbon atom (C*) of one of the fragments (A1 to A36) shown in Table 1 to the nitrogen atom (N*) of one of the fragments (B1 to B4) shown in Table 2, and joining the carbon atom (C*) of one of the fragments (B1 to B4) shown in Table 2 to the carbon atom (C*) of one of the acidic fragments (C3 to C32) depicted in Table 3.

TABLE 1

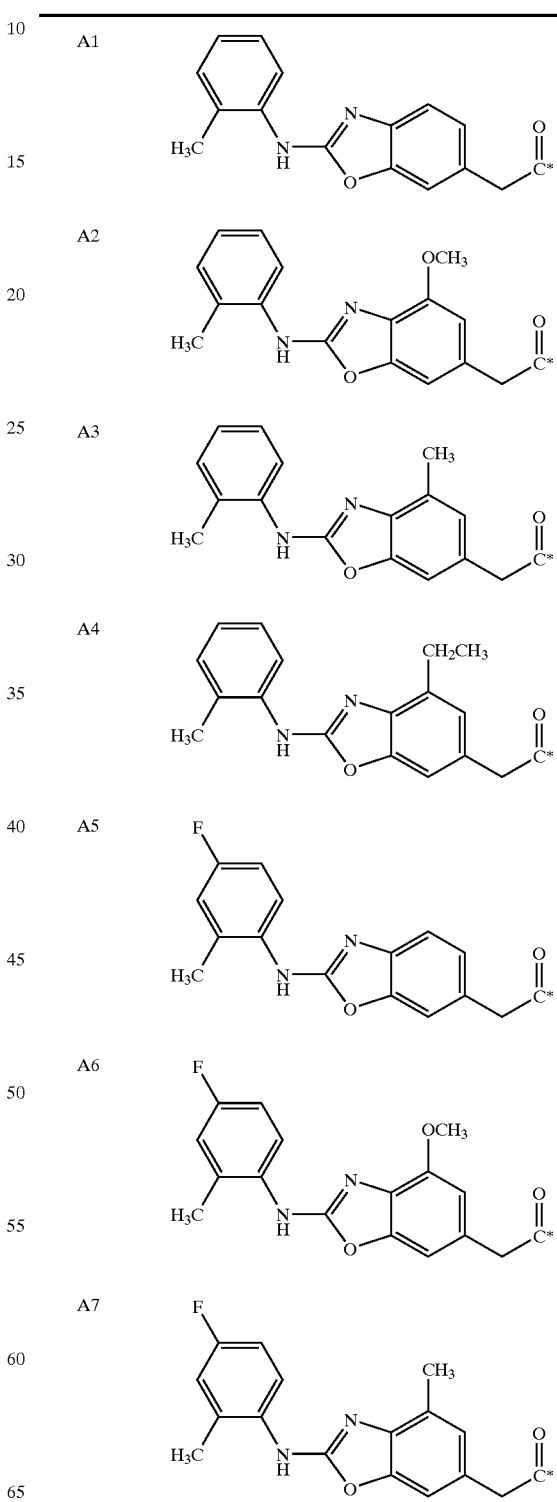

TABLE 1-continued
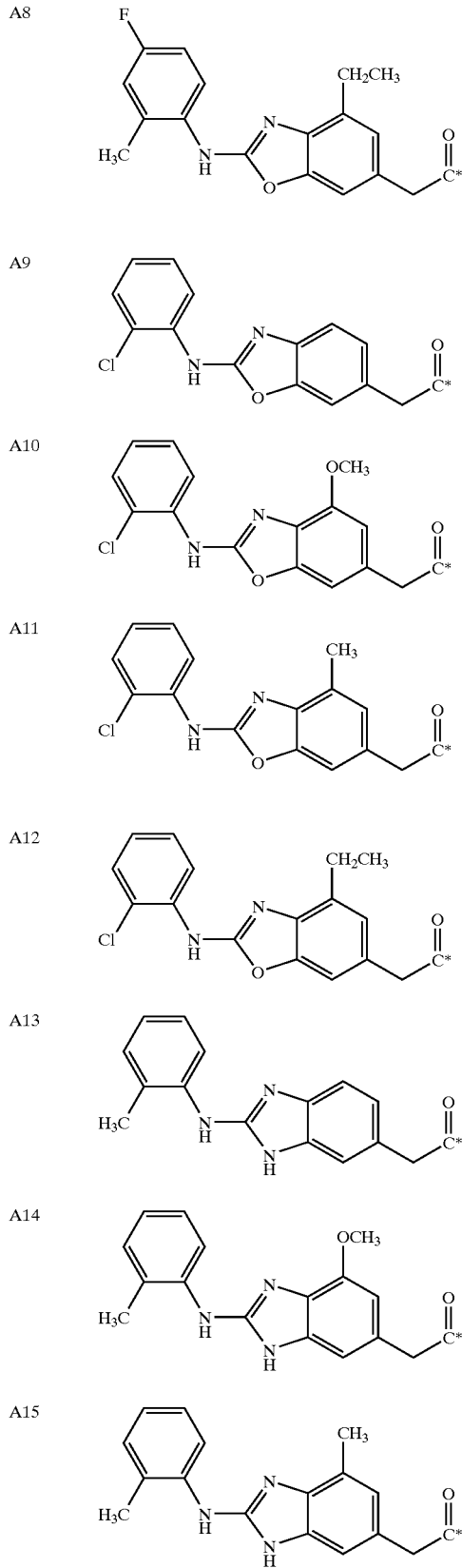
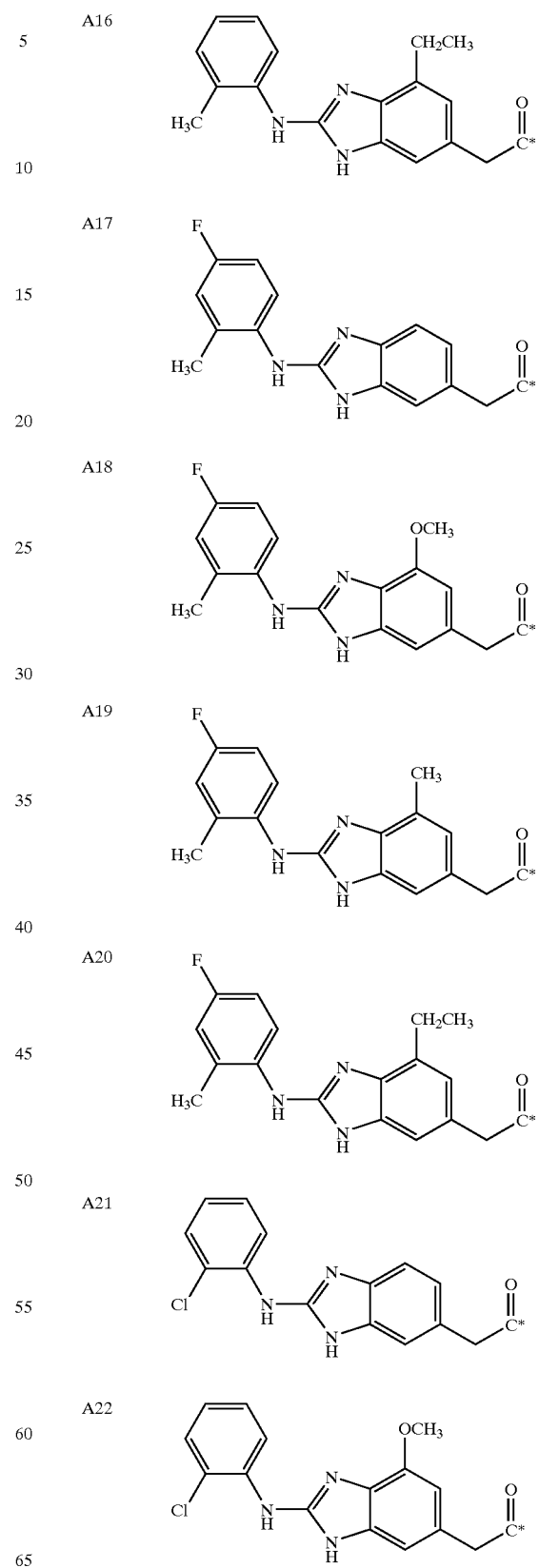

TABLE 1-continued
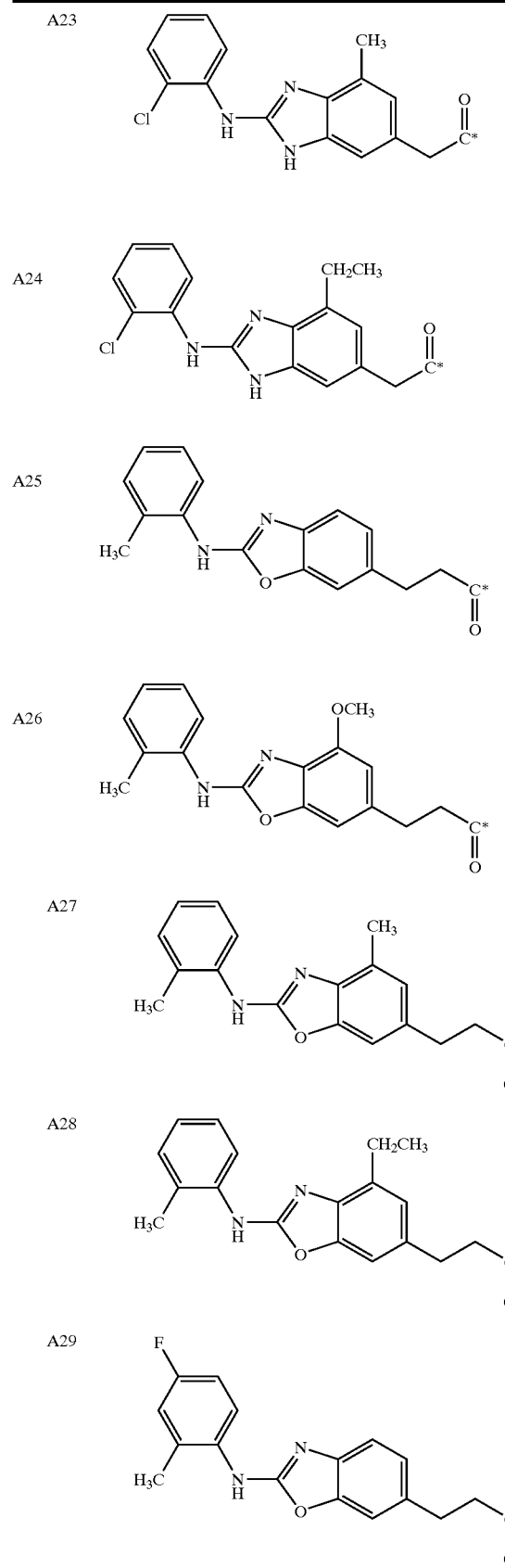
TABLE 1-continued
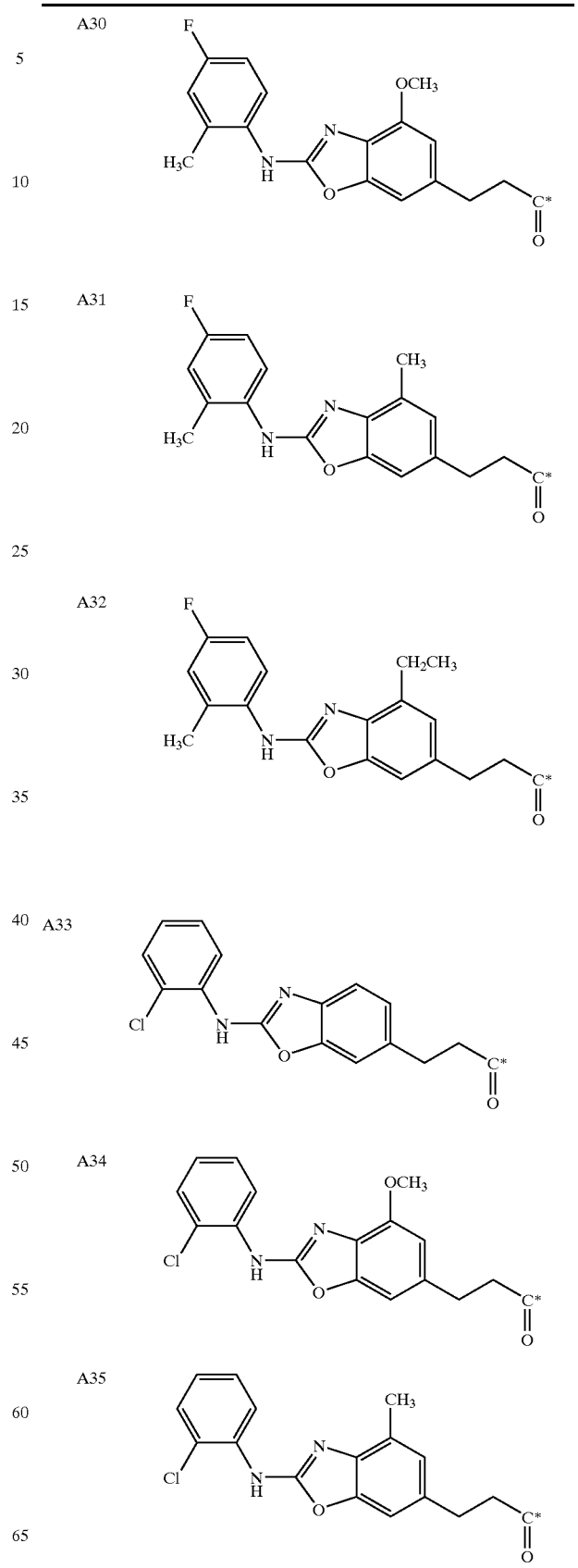

TABLE 1-continued
A36 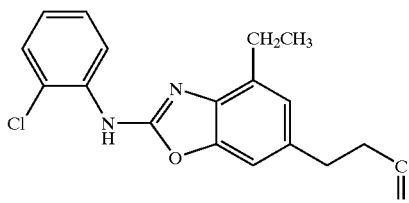
TABLE 2
B1 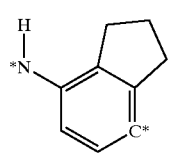
B2 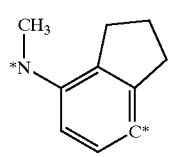
B3 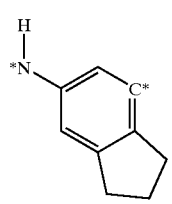
B4 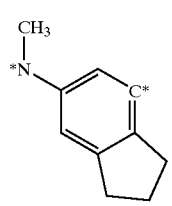
B5 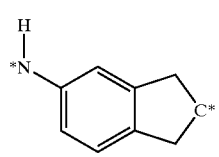
B6 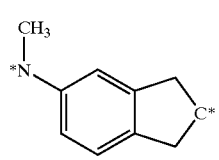
B7 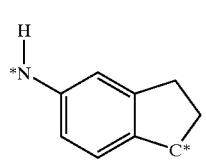
TABLE 2-continued
B8 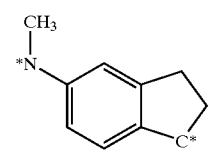
B9 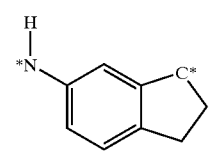
B10 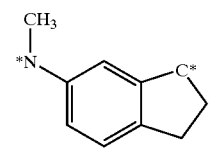
B11 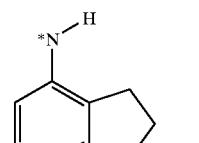
B12 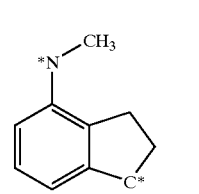
TABLE 3
| | |
|---|---|
| C1 | *CO$_2$H |
| C2 | *CH$_2$—CO$_2$H |
| C3 | *CH$_2$—CH$_2$CO$_2$H |
| C4 | *CH$_2$—CH$_2$—CH$_2$—CO$_2$H |
| C5 | 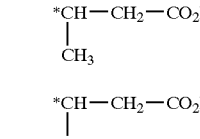 |
| C6 | 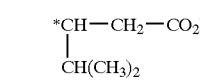 |
| C7 | 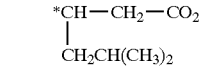 |
| C8 | 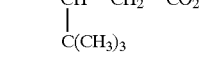 |
| C9 | 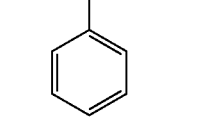 |
| C10 | 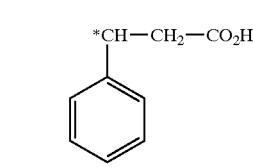 |

TABLE 3-continued

| | | |
|---|---|---|
| C11 | *CH—CH₂—CO₂H, 4-fluorophenyl | |
| C12 | *CH—CH₂—CO₂H, pyridin-2-yl | |
| C13 | *CH—CH₂—CO₂H, pyridin-3-yl | |
| C14 | *CH—CH₂—CO₂H, pyridin-4-yl | |
| C15 | *CH—CH₂—CO₂H, furan-3-yl | |
| C16 | *CH—CH₂—CO₂H, furan-2-yl | |
| C17 | *CH—CH₂—CO₂H, thiophen-3-yl | |
| C18 | *CH—CH₂—CO₂H, thiophen-2-yl | |
| C19 | *CH—CH₂—CO₂H, piperidin-1-yl | |
| C20 | *CH—CH₂—CO₂H, tetrahydropyran-4-yl | |
| C21 | *CH—CH₂—CO₂H, cyclopropyl (CH₂) | |
| C22 | cyclopentyl-*C—CH₂—CO₂H | |
| C23 | indan-2-yl-*C—CH₂—CO₂H | |
| C24 | *CH—CH₂—CO₂H, CH₂CO₂H | |
| C25 | *CH—CH₂—CO₂H, CH₂—C(=O)—N(pyrrolidin-1-yl) | |
| C26 | *CH—CH₂—CO₂H, OMe | |
| C27 | *CH—CH₂—CO₂H, HN—C(=O)—phenyl | |
| C28 | *CH₂—CH—CO₂H, HN—C(=O)—(2,6-dichlorophenyl) | |
| C29 | *CH₂—CH—CO₂H, HN—C(=O)—(2-methyl-6-chlorophenyl) | |

TABLE 3-continued

| | |
|---|---|
| C30 | *CH—CH₂—CO₂H, HN-C(=O)-(2-pyridyl) |
| C31 | *CH—CH₂—CO₂H, HN-C(=O)-(2-thienyl) |
| C32 | *CH—CH₂—CO₂H, HN-C(=O)-(5-methyl-isoxazol-3-yl) |

Examples of compounds in accordance with the present invention are those derived from all combinations of fragments "A", "B", and "C", and the corresponding N-oxides, and their prodrugs; and pharmaceutically acceptable salts and solvates (e.g. hydrates) of such compounds and their N-oxides and prodrugs.

Thus, for example, in the above list the compound denoted as A1-B1-C5 is the product of the combination of group A1 in Table 1 and B1 in Table 2 and C5 in Table 3, namely

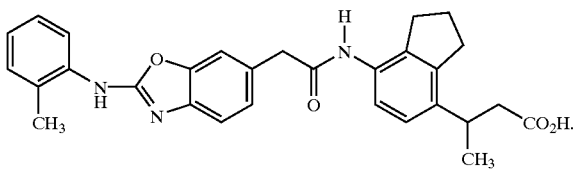

A preferred compound of the invention is:

3-{7-[2-(2-o-tolylamino-benzoxazol-6-yl)-acetylamino]-indan-4-yl}-butyric acid;

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 ($\alpha 4\beta 1$) according to tests described in the literature and described in vitro and in vivo procedures hereinafter, and which tests results are believed to correlate to pharmacological activity in humans and other mammals.

Thus, in a further embodiment, the present invention provides compounds of the invention and compositions containing compounds of the invention for use in the treatment of a patient suffering from, or subject to, conditions which can be ameliorated by the administration of an inhibitor of $\alpha 4\beta 1$ mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds may be useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of formula (I), wherein $R^1$, $R^2$ and $L^1$ are as hereinbefore defined, and where Y is carboxy, may be prepared by hydrolysis of esters of formula (I), wherein $R^1$, $R^2$ and $L^1$ are as hereinbefore defined and Y is a —$CO_2R^{19}$ group (in which $R^{19}$ is alkyl, alkenyl or arylalkyl). The hydrolysis may conveniently be carried out by alkaline hydrolysis using a base, such as an alkali metal hydroxide, e.g. sodium hydroxide or lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient temperature to about reflux temperature. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I), wherein $R^1$, $R^2$ and $L^1$ are as hereinbefore defined, and where Y is carboxy, may be prepared by acid catalysed removal of the tert-butyl group of tert-butyl esters of formula (I), wherein $R^1$, $R^2$ and $L^1$ are as hereinbefore defined and Y is a —$CO_2R^{19}$ group (in which $R^{19}$ is tert-butyl), using standard reaction conditions, for example reaction with trifluoroacetic acid at a temperature at about room temperature.

As another example compounds of formula (I), wherein $R^1$, $R^2$ and $L^1$ are as hereinbefore defined, and where Y is carboxy, may be prepared by hydrogenation of compounds of formula (I) wherein $R^1$, $R^2$ and $L^1$ are as hereinbefore defined and Y is a —$CO_2R^{19}$ group (in which $R^{19}$ is arylmethyl, e.g. benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol. This reaction is most suitable for compounds of formula (I) where $L^1$ does not contain carbon-carbon multiple bonds.

In a process A compounds of formula (I), containing an amide bond may be prepared by coupling of an acid (or an acid halide) with an amine to give an amide bond using standard peptide coupling procedures as described hereinafter.

As an example of process A, esters of formula (I), wherein $R^1$, $R^2$ and $L^1$ are as hereinbefore defined, and Y is a —$CO_2R^{19}$ group (in which $R^{19}$ is as hereinbefore defined), may be prepared by reacting a compound of formula (II):

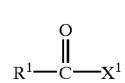

(II)

wherein $R^1$ is as hereinbefore defined and $X^1$ is a hydroxy group, or a halogen, preferably chlorine, atom with an amine of formula (III):

(III)

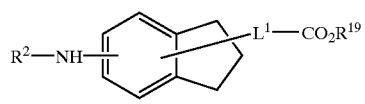

wherein $R^2$, $R^{19}$ and $L^1$ are as hereinbefore defined, the group $R^2$—NH— is attached to the benzene ring of the indane system and the group —$L^1$—$CO_2R^{19}$ is attached to either ring of the indane system, using standard coupling conditions. For example when $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature.

As another example of process A, compounds of formula (I) wherein $R^1$, $R^2$ and $L^1$ are as hereinbefore defined, and Y is carboxy, may be prepared by:

(i) treating bromo-Wang resin (4-bromomethylphenoxylated styrene/divinylbenzene copolymer) with an acid of formula (IV) wherein $R^2$ and $L^1$ are as hereinbefore defined, $R^{20}$ is a suitable imino-protecting group, such as 9H-fluoren-9-ylmethoxylcarbonyl, the group

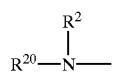

is attached to the benzene ring of the indane system and the group —$L^1$—$CO_2H$ is attached to either ring of the indane system, in the presence of a tertiary amine, such as diisopropylethylamine, and cesium iodide, in an inert solvent, such as dimethylformamide, at a temperature at about room temperature, to give Resin A:

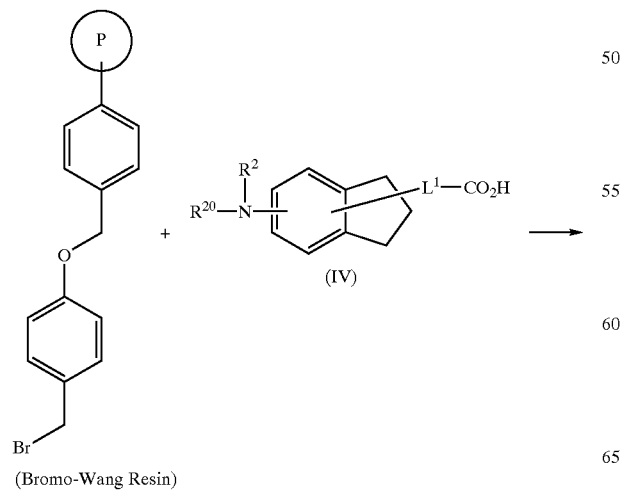

(Bromo-Wang Resin)

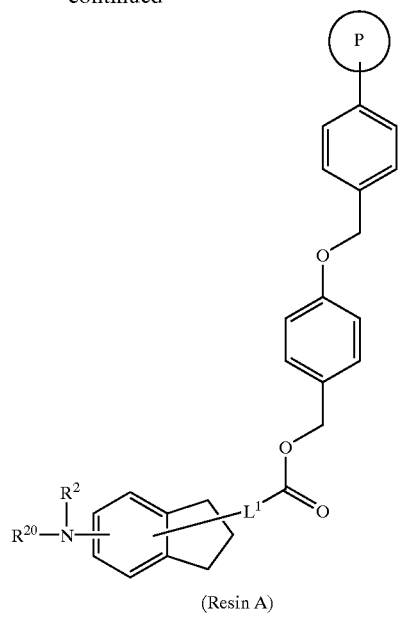

(Resin A)

where

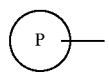

represents the polymeric core comprising polystyrene crosslinked with 1% to 2% divinylbenzene;

(ii) treatment of Resin A with piperidine in an inert solvent, such as dimethylformamide, and at a temperature at about room temperature to give Resin B:

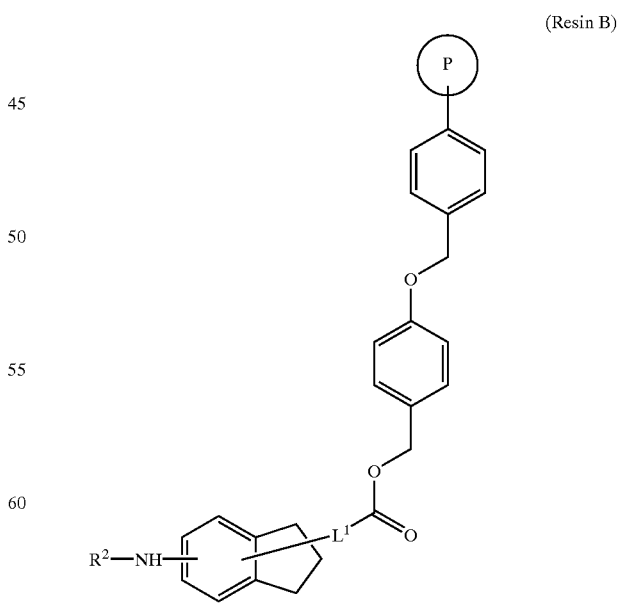

(Resin B)

wherein $R^2$, $L^1$ and

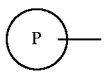

are as hereinbefore defined;

(iii) Reaction of Resin B with compounds of formula (II) wherein $R^1$ and $X^1$ are as hereinbefore defined, using standard coupling procedures (for example those described hereinabove), to give Resin C:

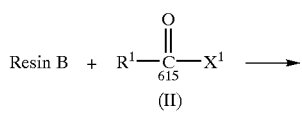

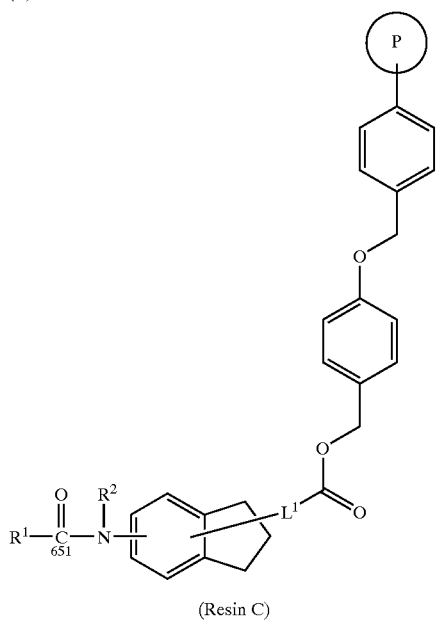

(Resin C)

wherein $R^1$, $R^2$ $L^1$ and

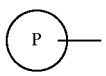

are as hereinbefore defined;

(iv) treatment of Resin C with trifluoroacetic acid in an inert solvent, such as dichloromethane, and at a temperature at about room temperature.

As another example of process A, esters of formula (I), wherein $R^1$ and $R^2$ are as hereinbefore defined, Y is a —$CO_2R^{19}$ group (in which $R^{19}$ is as hereinbefore defined) and $L^1$ contains a —$N(R^6)$—$C(=O)$—$R^4$ group (in which $R^6$ and $R^4$ are as hereinbefore defined) may be prepared by reaction of the corresponding compounds of formula (I) wherein $R^1$, $R^2$ and Y are as hereinbefore defined and $L^1$ contains a —$NH(R^6)$ group (in which $R^6$ is as hereinbefore defined) with acids (or acid chlorides) of formula (V):

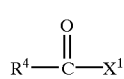
(V)

wherein $R^4$ and $X^1$ are as hereinbefore defined, using standard coupling conditions, for example those described hereinbefore.

Esters of formula (I), wherein $R^1$ and $R^2$ are as hereinbefore defined, Y is a —$CO_2R^{19}$ group (in which $R^{19}$ is as hereinbefore defined) and $L^1$ contains a —$NHR^6$ group (in which $R^6$ is alkyl, arylalkyl, cycloalkylalkyl, heteroarylalkyl or heterocycloalkylalkyl), may be prepared by alkylation of the corresponding derivatives of formula (I) where $L^1$ contains a —$NH_2$ group, with the appropriate alkyl (or arylalkyl, cycloalkylalkyl, heteroarylalkyl or heterocycloalkylalkyl) halide. The alkylation may for example be carried out in the presence of a base, such as an alkali metal hydride, e.g. sodium hydride, in dimethylformamide, or dimethyl sulfoxide, at a temperature from about 0° C. to about 100° C.

Esters of formula (I), wherein $R^1$ and $R^2$ are as hereinbefore defined, Y is a —$CO_2R^{19}$ group (in which $R^{19}$ is as hereinbefore defined) and $L^1$ contains a —$N(R^6)$—$C(=O)$—$OR^4$ group (in which $R^6$ and $R^4$ are as hereinbefore defined), may be prepared from the corresponding derivatives of formula (I) where $L^1$ contains a —$NHR^6$ group (in which $R^6$ is as hereinbefore defined) by reaction with compounds of formula $R^4O$—$C(=O)$—$X^2$ wherein $R^4$ and $X^2$ is a halogen, preferably chlorine atom, or —O—$C(=O)$—$OR^4$ in the presence of a suitable base, such as triethylamine or pyridine, and at a temperature from about 0° C. to about room temperature.

Esters of formula (I), wherein $R^1$ and $R^2$ are as hereinbefore defined, Y is a —$CO_2R^{19}$ group (in which $R^{19}$ is as hereinbefore defined) and $L^1$ is

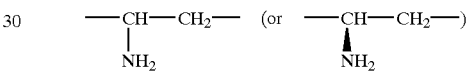

may be prepared by hydrogenation of the corresponding derivatives of formula (I), where $L^1$ is

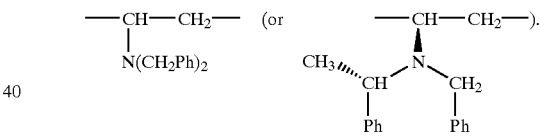

The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein $R^1$ and $R^2$ are as hereinbefore defined, Y is a —$CO_2R^{19}$ group (in which $R^{19}$ is as hereinbefore defined) and $L^1$ is a

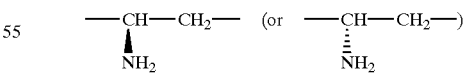

linkage, may also be obtained from the racemic mixture following standard recrystallisation of a suitable salt (for example recrystallisation of the tartrate salt), or by the application of standard enzymatic resolution procedures (for example those described by Soloshonok, V. A., et. al., Tetrahedron: Asymmetry 6 (1995) 7, 1601–1610).

Esters of formula (I), wherein $R^1$ and $R^2$ are as hereinbefore defined, Y is a —$CO_2R^{19}$ group (in which $R^{19}$ is as hereinbefore defined) and $L^1$ is a

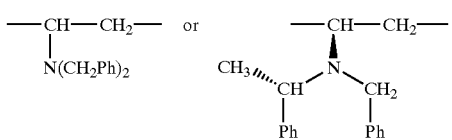

linkage, may be prepared by reacting an ester of formula (I), wherein $R^1$ and $R^2$ are as hereinbefore defined, Y is a —$CO_2R^{19}$ group (in which $R^{19}$ is as hereinbefore defined) and $L^1$ is a —CH=CH— linkage, with an alkali metal hydride, such as sodium hydride, in an inert solvent, e.g. tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

Lactones of formula (I) wherein $R^1$ and $R^2$ are as hereinbefore defined and the moiety —$L^1$—Y is

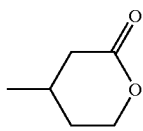

may be prepared by the selective reduction (using for example a borane derivative or lithium borohydride) of compounds of formula (I) wherein $R^1$ and $R^2$ are as hereinbefore defined and the moiety —$L^1$—Y is

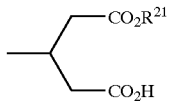

(in which $R^{21}$ is lower alkyl) followed by spontaneous cyclisation of the intermediate hydroxy compound. The reduction can be achieved by the application or adaptation of the procedures described by C. J. Francis and J. Bryan Jones, J. Chem. Soc, Chem. Commun., 1984, (9), 579–58, J. Hiratake et al, J. Chem. Soc, Perkin Trans, 1987, 1 (5), 1053–8 L. K. P. Lamet al, J. Org. Chem. (1986), 51(11), 2047–50.

Lactones of formula (I) wherein $R^1$ and $R^2$ are as hereinbefore defined and the moiety —$L^1$—Y is

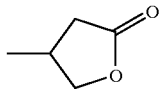

may be similarly prepared from compounds of formula (I) wherein $R^1$ and $R^2$ are as hereinbefore defined and the moiety —$L^1$—Y is

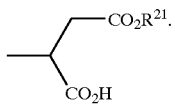

According to a further feature of the present invention, compounds of the invention may be prepared by interconversion of other compounds of the invention.

For example compounds of formula (I), wherein $R^1$, $R^2$ and $L^1$ are as hereinbefore defined, and Y is a group —C(=O)—NHOH, may be prepared by reacting compounds of formula (I), wherein $R^1$, $R^2$ and $L^1$ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl) hydroxylamine, O-(t-butyldimethylsilyl)-hydroxylamine, or O-(tetrahydropyranyl)hydroxylamine followed by treatment with acid.

As another example of the interconversion process, compounds of formula (I) containing sulfoxide linkages may be prepared by the oxidation of corresponding compounds containing —S— linkages. For example, the oxidation may conveniently be carried out by means of reaction with a peroxyacid, e.g. 3-chloroperbenzoic acid, preferably in an inert solvent, e.g. dichloromethane, preferably at or near room temperature, or alternatively by means of potassium hydrogen peroxomonosulfate in a medium such as aqueous methanol, buffered to about pH 5, at temperatures between about 0° C. and room temperature. This latter method is preferred for compounds containing an acid-labile group.

As another example of the interconversion process, compounds of formula (I) containing sulfone linkages may be prepared by the oxidation of corresponding compounds containing —S— or sulfoxide linkages. For example, the oxidation may conveniently be carried out by means of reaction with a peroxyacid, e.g. 3-chloroperbenzoic acid, preferably in an inert solvent, e.g. dichloromethane, preferably at or near room temperature.

As another example of the interconversion process, compounds of formula (I), wherein $R^1$, $R^2$ and Y are as hereinbefore defined, and $L^1$ is optionally substituted alkylene, may be prepared by hydrogenation of the corresponding compounds of formula (I) in which $L^1$ is the corresponding optionally substituted alkenylene. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I), wherein $R^1$ and $R^2$ are as hereinbefore defined, $L^1$ is an alkylene linkage substituted by —$CONY^3Y^4$ and Y is carboxy, may be prepared by reacting compounds of formula (I), wherein $R^1$ and $R^2$ are as hereinbefore defined, $L^1$ is an alkylene linkage substituted by —$CO_2H$ and Y is carboxy, with an anhydride, such as trifluoroacetic anhydride, in an inert solvent e.g. tetrahydrofuran, followed by treatment with an amine $HNY^3Y^4$.

As another example of the interconversion process, compounds of formula (I) wherein $R^1$ and $R^2$ are as hereinbefore defined, $L^1$ is a

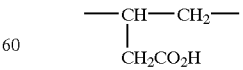

linkage and Y is carboxy, may be prepared by (i) reacting an ester of formula (I) wherein $R^1$ and $R^2$ are as hereinbefore defined, $L^1$ is a —CH=CH— linkage and Y is —$CO_2R^{19}$ (in which $R^{19}$ is as hereinbefore defined) with dimethyl malonate, in the presence of an alkali metal alkoxide, such as sodium methoxide, in methanol and at a temperature at about reflux temperature and (ii) treatment of the resulting compounds of formula (I) wherein $R^1$ and $R^2$ are as hereinbefore defined, $L^1$ is a

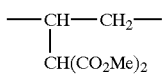

linkage and Y is —$CO_2R^{19}$ with hydrochloric acid at reflux temperature.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Acids of formula (II) wherein $R^1$ is a group $R^3$—$L^2$—$Ar^1$—$L^3$—[in which $R^3$ and $L^3$ are as defined hereinbefore, $L^2$ is NH, $Ar^1$ is

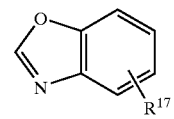

(in which $R^{17}$ is as hereinbefore defined] and $X^1$ is a hydroxy group may be prepared by: (i) reaction of compounds of formula (1):

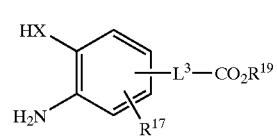

(1)

wherein $R^{17}$, $R^{19}$ and $L^3$ are as hereinbefore defined and X is O, with isothiocyanates of formula $R^3$—N=S=O (in which $R^3$ is as hereinbefore defined) in ethanol and at room temperature; (ii) reaction with a carbodiimide, such as dicyclohexylcarbodiimide or diisopropylcarbodiimide in ethanol and at a temperature from about room temperature to about reflux temperature and (iii) acidic or alkaline hydrolysis of the esters where for example $R^{19}$ is alkyl, hydrogenolysis of the esters where for example $R^{19}$ is benzyl or acid catalysed removal of the tert-butyl group of the esters where $R^{19}$ is tert-butyl using standard reaction conditions for example those described hereinbefore.

Acids of formula (II) wherein $R^1$ is a group $R^3$—$L^2$—$Ar^1$—$L^3$— (in which $R^3$ and $L^3$ are as hereinbefore defined, $Ar^1$ is

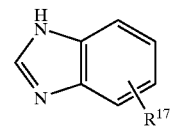

(in which $R^{17}$ is as hereinbefore defined), $L^2$ is NH and $X^1$ is hydroxy may be similarly prepared from compounds of formula (1) wherein $R^{17}$, $R^{19}$ and $L^3$ are as hereinbefore defined and X is NH.

Acid chlorides of formula (II) wherein $R^1$ is as hereinbefore defined and $X^1$ is a chlorine atom may be prepared from the corresponding acids of formula (II) wherein $R^1$ is as hereinbefore defined and $X^1$ is hydroxy, by the application of standard procedures for the conversion of acids to acid chlorides for example by reaction with oxalyl chloride.

Compounds of formula (III) wherein $R^{19}$ and $L^1$ are as hereinbefore defined, $R^2$ is hydrogen, the $R^2$—NH— group is attached to the benzene ring of the indane system and the group —$L^2$—Y is attached to either ring of the indane system, may be prepared by reduction of the corresponding nitro compounds of formula (2):

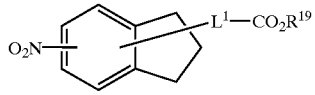
(2)

wherein $R^{19}$ and $L^1$ are as defined hereinbefore, the nitro group is attached to the benzene ring of the indane system and the group —$L^2$—Y is attached to either ring of the indane system. For compounds of formula (III) in which $R^{19}$ is alkyl and $L^1$ is an optionally substituted alkylene linkage the reduction may conveniently be carried out by hydrogenation of the corresponding nitro compounds of formula (2) wherein $R^{19}$ is as just defined and $L^1$ is the corresponding optionally substituted alkylene or alkenylene linkage, using standard hydrogenation conditions, for example those described hereinbefore. For compounds of formula (III) in which $R^{19}$ is benzyl the reduction may conveniently be carried out using iron powder and ammonium chloride, in aqueous ethanol at a temperature at about reflux, or tin (II) chloride in the presence of hydrochloric acid, at a temperature up to about 80° C.

Compounds of formula (III) wherein $R^{19}$ and $L^1$ are as hereinbefore defined, $R^2$ is hydrogen, the $R^2$—NH— group is attached to the benzene ring of the indane system and the group —$L^2$—$CO_2R^{19}$ is attached to either ring of the indane system may be prepared by reaction of compounds of formula (3):

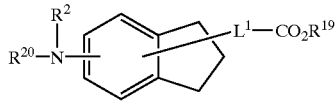
(3)

wherein $R^2$, $R^{19}$ and $L^1$ are as just defined and $R^{20}$ is an acid-labile protecting group (e.g. acetyl), the

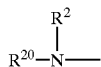

group is attached to the benzene ring of the indane system and the group —$L^2$—$CO_2R^{19}$ is attached to either ring of the indane system, with hydrochloric acid and at a temperature at about reflux temperature followed by re-esterification using standard esterification procedures [for example when $R^{19}$ is alkyl the esterification may conveniently be prepared following reaction with an alkyl alcohol (e.g. methanol) in the presence of an acid catalyst, such as hydrogen chloride or sulfuric acid at a temperature from about room temperature to about reflux temperature]. This method is particularly suitable for the preparation of compounds of formula (III) where $R^2$ is hydrogen and both the $R^2$—NH— and the $L^1$—$CO_2R^{19}$ group are attached to the benzene ring of the indane system.

Compounds of formula (III) wherein $R^{19}$ and $L^1$ are as hereinbefore defined and $R^2$ is methyl may be prepared by treatment of compounds of formula (III) wherein $R^{19}$ and $L^1$ are as hereinbefore defined and $R^2$ is hydrogen with formic acetic anhydride followed by reduction with lithium aluminium hydride according to the procedure described by L. G. Humber L G et al, J Med Chem., 1971, 14, page 982.

Compounds of formula (2) wherein $R^{19}$ and $L^1$ are as defined hereinbefore may be prepared by esterification of acids of formula (4):

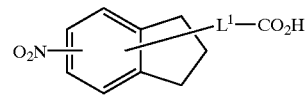
(4)

wherein $L^1$ is as defined hereinbefore, the nitro group is attached to the benzene ring of the indane system and the group —$L^2$—$CO_2H$ is attached to either ring of the indane system, using standard esterification procedures as described hereinbefore.

Compounds of formula (4) wherein $L^1$ are as defined hereinbefore and the nitro group is attached to the benzene ring of the indane system, may be prepared by nitration of compounds of formula (5):

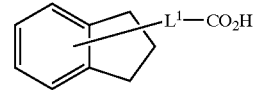
(5)

wherein $L^1$ are as defined hereinbefore and the group —$L^2$—$CO_2H$ is attached to either ring of the indane system, with concentrated nitric acid in the presence of acetic acid and acetic anhydride at a temperature at about 5° C. This method is particularly suitable for the preparation of compounds of formula (4) where the —$L^1$—$CO_2H$ group are attached to the cyclopentyl ring of the indane system.

Compounds of formula (IV) wherein $R^2$, $R^{20}$ and $L^1$ are as defined hereinbefore, may be prepared from the corresponding esters of formula (3) wherein $R^2$, $R^{19}$, $R^{20}$ and $L^1$ are as hereinbefore defined using standard reaction conditions, for example those described hereinbefore (acidic or alkaline hydrolysis of the esters where for example $R^{19}$ is alkyl, hydrogenolysis of the esters where for example $R^{19}$ is benzyl or acid catalysed removal of the tert-butyl group of the esters where $R^{19}$ is tert-butyl).

Compounds of formula (3) wherein $R^2$ and $R^{19}$ are as hereinbefore defined, $R^{20}$ is a suitable protecting group (e.g. acetyl) and $L^1$ is alkenylene, alkynylene or cycloalkenylene attached to the benzene ring of the indane system, may be prepared by reaction compounds of formula (6):

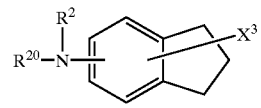
(6)

wherein $R^2$ and $R^{20}$ are as just defined and $X^3$ is a halogen atom attached to the benzene ring of the indane system, with a compound of formula (7)

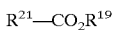
(7)

wherein $R^{19}$ is as hereinbefore defined and $R^{21}$ is alkenyl, alkynyl or cycloalkenyl. When $X^3$ is a bromine or iodine atom the reaction may be conveniently carried out in the presence of palladium acetate, a triarylphosphine, such as tri-o-tolylphosphine, and a tertiary amine, such as tributylamine, at a temperature up to about 110° C. This reaction is particularly suitable for the preparation of esters of formula (I) in which $L^1$ is vinylene. When $X^3$ is a chlorine atom the reaction may be conveniently carried out in the presence of sodium iodide, nickel bromide, palladium(0) bis(dibenzylideneacetone), a triarylphosphine, such as tri-o-tolylphosphine, and a tertiary amine, such as tributylamine, at a temperature up to about 110° C.

Compounds of formula (3) wherein $R^2$ and $R^{20}$ are as defined hereinbefore, $R^{19}$ is alkyl and $L^1$ is alkylene or cycloalkylene, may be prepared by hydrogenation of the corresponding compounds of formula (3) wherein $L^1$ is alkenylene, alkynylene or cycloalkenylene, using standard hydrogenation conditions as described hereinbefore.

Compounds of formula (3) wherein $R^2$, $R^{19}$ and $R^{20}$ are as defined hereinbefore and $L^1$ is

may be prepared by reaction of compounds of formula (8):

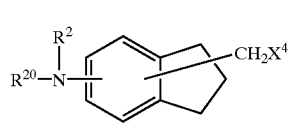

(8)

wherein $R^2$, $R^{20}$ and $Ar^1$ are as defined hereinbefore, $X^4$ is a bromine or chlorine atom, with the anion derived from reaction of (2R) -(−)-2,5-dihydro-3,6-dimethoxy-2-isopropylpyrazine with butyllithium according to the method described by D. L. Boger and D. Yohannes, J. Org. Chem. [JOCEAH], 1990, 55, for the preparation of compound 31 on page 6010.

Compounds of formula (5) wherein $L^1$ is methylene, substituted by —NH—C(=O)—$R^4$, and attached to the indane ring may be prepared by the application or adaptation of the methods described by Burk et. al., J. Amer. Chem. Soc., 1995, 117, pages 9375–9376.

Compounds of formula (5) wherein $L^1$ is alkylene attached to the indane ring may be prepared by: (i) reaction of indanone with the appropriate ester of formula (9):

$$Br-L^1-CO_2R^{21} \qquad (9)$$

wherein $R^{21}$ is as hereinbefore defined and $L^1$ is alkylene in the presence of zinc according to the procedure described by Campbaell et. al., Org. Prep. Proced. Int., 1991, 23, pages 660–665; (ii) dehydration of the resulting hydroxy-indane in the presence of sulfuric acid; (iii) hydrogenation of the resulting indene.

Compounds of formula (6) wherein $R^2$ is hydrogen, $R^{20}$ is acetyl, $X^3$ is a halogen atom and both the $X^3$ and

groups are attached to the benzene ring of the indane system, may be prepared by the application or adaptation of the methods described by A. Courtin, Helv. Chim. Acta., 1980, 63, pages 2280–2286.

Intermediates of formulae (IV) and (3) are novel compounds and, as such, they and their processes described herein for their preparation constitute further features of the present invention.

High Pressure Liquid Chromatography/Mass Spectrometry (LC/MS) conditions for determination of retention times ($R_T$) were as follows: 3 micron Luna C18 (2) HPLC column (30 mm×4.6 mm) operated under gradient elution conditions with mixtures of (A) water containing 0.1% formic acid and (B) acetonitrile containing 0.1% formic acid as the mobile phase gradient: 0.00 minutes, 95% A:5% B; 0.50 minutes, 95% A:5% B; 4.50 minutes, 5% A:95% B; 5.00 minutes, 5% A:95% B; 5.50 minute 95% A:5% B; flow rate 2 ml/minute with approximately 200 µl/minute split to the Mass Spectrometer; injection volume 10–40 µl; in line Diode Array (220–450 nm), in line Evaporative light scattering (ELS) detection ELS—temperature 50° C., Gain 8–1.8 ml/minute; Source temperature 150° C.

EXAMPLE 1

3-{7-[2-(2-o-Tolylamino-benzoxazol-6-yl)-acetylamino]-indan-4-yl}-butyric Acid

A solution of ethyl 3-{7-[2-(2-o-tolylamino-benzoxazol-6-yl)-acetylamino]-indan-4-yl}-butanoat [0.754 g, Reference Example 1(a)] in ethanol (150 mL) was treated with aqueous sodium hydroxide solution (4 mL, 1M). The reaction mixture was allowed to stand at room temperature for 48 hours, then heated at reflux temperature for 1 hour and then evaporated. The residue was dissolved in a mixture of acetonitrile and water (35:65, v/v) and the resulting solution was acidified to pH 2 by addition of trifluoroacetic acid. The resulting solid was filtered and subjected to reversed phase HPLC (Hypersil Elite C18 column, 10×2 cm, using acetonitrile and water mixtures containing 0.1% trifluoroacetic acid and running a linear gradient of +1% acetonitrile/minute, starting with 35% acetonitrile) to give the title compound (396 mg) as a white solid. LC-MS: $R_T$=3.37 minutes (>98% by ELSD); MS(ES$^+$), 484(MH$^+$).

EXAMPLE 2

(5-[2-{2-o-Tolylamino-benzoxazol-6-yl}-acetylamino]-indan-2-yl)-acetic Acid

A stirred solution of (2-o-tolylamino-benzoxazol-6-yl)-acetic acid (0.64 g, Reference Example 2) in dimethylformamide (5 mL) was treated successively with diisopropylethylamine (0.59 g), O-7-azabenzotriazol-1-yl)-1,1,3,3,-tetramethyluronium hexafluorophosphate (0.95 g), and a solution of ethyl (5-amino-indan-2-yl)-acetate [0.5 g, Reference Example 8(a)] in dimethylformamide (2.5 mL). After stirring at room temperature overnight the reaction was evaporated and the residual oil was dissolved in ethyl acetate. The ethyl acetate solution was washed twice with dilute hydrochloric acid, then with aqueous sodium bicarbonate, then with water and then evaporated. The residue was dissolved in industrial methylated spirits (100 mL) and the solution was treated with 3 equivalents of aqueous sodium hydroxide. After stirring at room temperature overnight (HPLC showed that none of the intermediate ester remained) the reaction mixture was evaporated. The residue was partitioned between ethyl acetate and water (with the pH of the aqueous layer adjusted to 2 by addition of dilute hydrochloric acid). The organic phase was dried over magnesium sulfate then evaporated. The residual brown gum was recrystallised from a mixture of acetonitrile and water at pH 2, then from acetonitrile after treatment with charcoal to give the title compound (0.050 g). LC-MS: $R_T$=3.21 minutes (100% by ELSD); MS(ES$^+$) 456(MH$^+$).

EXAMPLE 3

{5-[2-(2-o-Tolylamino-benzoxazol-6-yl)-acetylamino]-indan-1-yl}-acetic Acid

A solution of ethyl {5-[2-(2-o-tolylamino-benzoxazol-6-yl)-acetylamino]-indan-1-yl}-acetate [0.255 g, Reference Example 1(b)] in ethanol, under a nitrogen atmosphere, was treated with sodium hydroxide solution (1.6 mL, 1M) and the mixture was heated at reflux temperature for 1.5 hour. The reaction mixture was evaporated and the residual orange oil was treated with water (20 ml) and a few drops of tetrahydrofuran. The mixture was filtered and the filtrate was acidified to pH 1 by addition of concentrated hydrochloric acid. The resulting precipitate was filtered at 0° C., then washed twice with a little water and then dried in a dessicator at 50° C. to give the title compound (0.239 g) as a cream coloured solid. LC-MS: $R_T$=3.22 minutes (100% by ELSD); MS(ES$^+$) 456(MH$^+$), 478(MNa$^+$)

REFERENCE EXAMPLE 1

(a) Ethyl 3-{7-[2-(2-o-tolylamino-benzoxazol-6-yl)-acetylamino]-indan-4-yl}-butanoate A mixture of 2-(2-o-tolylamino-benzoxazol-6-yl)acetic acid (0.398 g, Reference Example 2), O-(7-azabenzotriazol-1-yl)-1,1,3,3-tetramethyluronium hexafluorophosphate (0.59 g) and diisopropylethylamine (0.24 g) in dimethylformamide was stirred at room temperature for 10 minutes and then treated with a solution of ethyl 3-[7-amino-indan-4-yl]-butanoate hydrochloride (0.4 g, Reference Example 5) in dimethylformamide. After shaking and then allowing to stand at room temperature for 16 hours the reaction mixture was evaporated under high vacuum. The residual red oil was dissolved in ethyl acetate and the solution was washed with 5% aqueous sodium bicarbonate, then with water, then dried over sodium sulfate and then evaporated to give the title compound (0.754 g) as an oil.

(b) By proceeding in a similar manner to Reference Example 1(a) but using ethyl (5-aminoindan-1-yl)-acetate [Reference Example 8(b)] and subjecting the crude reaction product to flash chromatography on silica, eluting with a mixture of ethyl acetate and pentane (initially 2:3 and then 1:1, v/v), there was prepared ethyl {5-[2-(2-o-tolylamino-benzoxazol-6-yl)-acetylamino]-indan-1-yl}-acetate (0.26 g) as a white solid.

REFERENCE EXAMPLE 2

(2-o-Tolylamino-benzoxazol-6-yl)-acetic Acid

A mixture of ethyl 4-amino-3-hydroxy-phenylacetate (3.3 g, Reference Example 3) and o-tolylisothiocyanate (2.5 mL) in ethanol (150 mL) was stirred at room temperature for about 2 hours. After standing at room temperature overnight the mixture was evaporated and the residue was subjected to flash chromatography on silica eluting with a mixture of pentane and ethyl acetate (7:3, v/v) to give a yellow foam. A solution of this material in ethanol (150 mL) was treated with dicyclohexylcarbodiimide (3.0 g) and the mixture was heated at reflux temperature for 2 hours. The mixture was evaporated and the residue subjected to short column chromatography on silica eluting with a mixture of 5–10% tert-butyl methyl ether in dichloromethane to remove dicyclohexylurea. The resulting light yellow oil was dissolved in ethanol (100 mL) and the solution was treated with sodium hydroxide solution (15 mL, 1M) then heated at reflux temperature for 2 hours. The reaction mixture was evaporated and the residue was dissolved in water. The solution was washed with ethyl acetate and the aqueous layer was acidified to pH 1 by addition of concentrated hydrochloric acid. The resulting white precipitate was collected by filtration, then washed thoroughly with water, and then dried to give the title compound (1.8 g) as a white solid.

REFERENCE EXAMPLE 3

Ethyl 4-amino-3-hydroxy-phenylacetate

A solution of ethyl 3-hydroxy-4-nitrophenylacetate (5 g, Reference Example 4) was dissolved in ethanol (approximately 200 mL) was treated with ammonium formate (approximately 20 g). The mixture was warmed to 50° C. and then treated cautiously with palladium on charcoal (approximately Ig, 5%)—effervescence was observed. After 30 minutes the mixture was filtered hot through a pad of celite and the filtrate was concentrated to give the title compound (3.3 g) as a black solid.

REFERENCE EXAMPLE 4

Ethyl 3-hydroxy-4-nitrophenylacetate

A solution of 3-hydroxy-4-nitrophenylacetic acid (4 g, prepared according to the procedure described by Meyer et al, J. Med. Chem., 1997, 40, pages 1049–1062) in ethanol (approximately 100 mL) was treated with concentrated hydrochloric acid (5–8 drops) was heated at reflux temperature for 3 hours then evaporated. The residue was dissolved in tert-butyl methylether and the solution was washed with saturated aqueous sodium bicarbonate solution, then with water, then dried, and then evaporated to give the title compound (5 g) as a light yellow solid.

REFERENCE EXAMPLE 5

Ethyl 3-[7-amino-indan-4-yl]-butanoate Hydrochloride

Ethyl 3-[7-acetylamino-indan-4-yl]-butanoate (1.66 g, Reference Example 6) was treated with 6M aqueous hydrochloric acid. The stirred mixture was heated at 118° C. for 4 hours, then left to stand at room temperature for 48 hours and then evaporated. The residue was treated with ethanol (100 mL) and concentrated hydrochloric acid (4 drops). This mixture was heated at reflux for 2.5 hours, then allowed to stand at room temperature for 16 hours and then evaporated. The residue was dissolved in a little ethanol and the solution was evaporated. The residue was dried under high vacuum to give the title compound (1.57 g) as a fine solid.

REFERENCE EXAMPLE 6

Ethyl 3-[7-acetylamino-indan-4-yl]-butanoate

A solution of ethyl 3-[7-acetylamino-indan-4-yl]-but-2-enoate (1.9 g, Reference Example 7) in ethanol (200 mL) was hydrogenated over 10% palladium on charcoal for 16 hours. The mixture was filtered through diatomaceous earth and the filtrate was evaporated to give the title compound (1.66 g).

REFERENCE EXAMPLE 7

Ethyl 3-[7-acetylamino-indan-4-yl]-but-2-enoate

A mixture of 4-acetylamino-7-bromoindane (2.8 g, prepared according to the method of A. Courtin, Helv. Chim. Acta 1980, 63(8), pages 2280–2286), ethyl crotonate (2.51 g), palladium diacetate (150 mg), tri-ortho-tolyl phosphine (450 mg) and tributylamine (10 mL) in dimethylformamide (30 mL) was stirred at 120° C. for 4 hours under a nitrogen atmosphere. The mixture was cooled to room temperature, then allowed to stand for 48 hours, then partitioned between ethyl acetate (500 mL) and aqueous hydrochloric acid (300 mL, 1M). The organic phase was washed with 5% aqueous sodium bicarbonate (150 mL) and then filtered. The clear yellow filtrate was dried over sodium sulfate then evaporated. The residue was subjected to normal phase HPLC on silica under gradient elution conditions using ethyl acetate, heptane and methanol mixtures (from 20:80:1 to 90/10/1, v/v/v) to give the title compound (1.9 g).

REFERENCE EXAMPLE 8

(a) Ethyl (5-amino-indan-2-yl)-acetate

A solution of (5-nitro-indan-2-yl)-acetic acid [2.22 g, Reference Example 9(a)] in ethanol (100 ml) containing sulfuric acid (5 drops) was refluxed for 4 hours, after which HPLC showed only a trace of free acid remaining. The mixture was treated with solid sodium bicarbonate to neutralise the sulfuric acid and then filtered. The filtrate was placed under a nitrogen atmosphere then 10% palladium on carbon (0.14 g) was added. The mixture was stirred rapidly and hydrogen was bubbled through the solution from a balloon. The reaction was monitored by HPLC until reduction was completed (4 hours) when the reaction mixture was filtered through a pad of celite. The filtrate was evaporated to give the title compound (2.16 g) as a dark red oil which was used without further purification.

(b) By proceeding in a similar manner to Reference Example 8(a) but using (5-nitroindan-1-yl)-acetic acid [Reference Example 9(b)] there was prepared ethyl (5-aminoindan-1-yl)-acetat

REFERENCE EXAMPLE 9

(a) (5-Nitro-indan-2-yl)-acetic Acid

Acetic anhydride (3.5 mL) was added slowly to a stirred solution of nitric acid (2.1 g, S.G.1.42) in glacial acetic acid (4.2 mL) cooled in an ice-water bath. This nitrating solution was then added dropwise over 5 minutes to a rapidly stirred solution of indan-2-acetic acid (1.65 g) in a mixture of glacial acetic acid (4.2 mL) and acetic anhydride (3.5 mL), whilst keeping the reaction temperature below 5° C. After stirring for a further 20 minutes at room temperature the reaction mixture was poured onto ice-water (60 mL). This mixture was extracted three times with dichloromethane. The combined extracts were washed twice with a little water, then dried over magnesium sulfate and then evaporated to give the title compound (2.22 g) as a red oil which was used without further purification.

(b) By proceeding in a similar manner to Reference Example 9(a) but using indan-1-acetic acid there was prepared (5-nitroindan-1-yl)-acetic acid.

In Vitro and In Vivo Test Procedures

1. Inhibitory Effects of Compounds on VLA4 Dependent Cell Adhesion to Fibronectin and VCAM 1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 µCi/100 mls of [$^3$H]-methionine (Amersham, UK) for 18 hours at 37° C.

1.2 96 Well Plate Preparation for Adhesion Assay

Cytostar plates (Amersham, UK) were coated with 50 µl/well of either 3 µg/ml human soluble VCAM-1 (R&D Systems Ltd, UK) or 28.8 µg/ml human tissue Fibronectin (Sigma, UK). In control non-specific binding wells 50 µl phosphate buffered saline was added. The plates were then left to dry in an incubator at 25° C., overnight. The next day the plates were blocked with 200 µl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 µl/well of 3.6% dimethyl sulfoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 µl /well of the test compounds at the appropriate concentrations diluted in 3.6% dimethyl sulfoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 µl/well of cells in 3.6% dimethyl sulfoxide in Pucks buffer and supplements was added to all plate wells.

The same procedure exists for plates coated with either VCAM-1 or fibronectin and data is determined for compound inhibition of cell binding to both substrates.

1.3 Performance of Assay and Data Analysis

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Compounds of the invention inhibit cell adhesion to fibronectin and VCAM-1 with $IC_{50}$'s in the range 100 micromolar to 100 nanomolar.

2. Inhibition of Antigen-induced Airway Inflammation in the Mouse and Rat 2.1 Sensitization of the Animals Rats (Brown Norway, Harland Olac, UK) are sensitized on days 0, 12 and 21 with ovalbumin (100 µg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 µg, i.p.) administered with aluminium hydroxide adjuvant (20 mg, i.p.) in saline (0.2 ml, i.p.).

2.2 Antigen Challenge

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalevolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK).

2.5 Data Analysis

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where p<0.05 no statistical significance existed.

What is claimed is:

1. A compound of general formula (I):

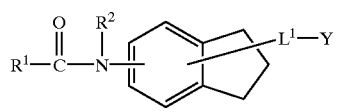

(I)

wherein:

R$^1$ represents a group R$^3$—L$^2$—Ar$^1$—L$^3$—;

R$^2$ represents hydrogen or lower alkyl;

R$^3$ represents an optionally substituted aryl group;

R$^8$ is hydrogen or lower alkyl;

Ar$^1$ represents an optionally substituted saturated, partially saturated or fully unsaturated 8 to 10 membered bicyclic ring system containing at least one heteroatom selected from O, S or N;

L$^1$ represents an alkylene, alkenylene or alkynylene linkage;

L$^2$ represents NR$^8$;

L$^3$ represents an alkylene, alkenylene or alkynylene chain; and

Y is carboxy or an acid bioisostere;

wherein the group

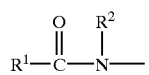

is attached to the benzene ring of the indane system and the group —L$^1$—Y is attached to either ring of the indane system;

and the corresponding N-oxides, and their prodrugs; and pharmaceutically acceptable salts and solvates of such compounds and their N-oxides and prodrugs.

2. A compound according to claim 1 wherein R$^3$ is a monosubstituted or disubstituted phenyl, and wherein the optional substituents are selected from C$_{1-4}$ alkyl, C$_{1-4}$ alkoxy and halo.

3. A compound according to claim 1 wherein L$^2$ is NH.

4. A compound according to claim 1 wherein Ar$^1$ represents an 8 to 10 membered bicyclic system

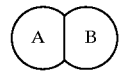

in which ring

is a 5 or 6 membered heteroaryl ring and ring

is a 5 or 6 membered heteroaryl ring or a benzene ring, each ring optionally substituted by one or more groups selected from aryloxy, cyano, halo. lower alkoxy, lower alkyl, nitro and perfluoroloweralkyl, and the two rings are joined together by a carbon-carbon linkage or a carbon-nitrogen linkage.

5. A compound according to claim 4 in which Ar$^1$ represents an optionally substituted 9 membered bicyclic system

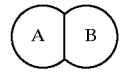

in which ring

is a 5 membered fully unsaturated heterocycle,

is an optionally substituted benzene and the two rings are joined together by a carbon-carbon linkage.

6. A compound according to claim 4 wherein

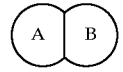

represents benzoxazolyl or benzimidazolyl, in which ring

is optionally substituted by one or more groups selected from C$_{1-4}$alkyl, C$_{1-4}$alkoxy, amino, halogen, hydroxy, C$_{1-4}$alkylthio, C$_{1-4}$alkylsulfinyl, C$_{1-4}$alkylsulfonyl, nitro and trifluoromethyl.

7. A compound according to claim 1 wherein L$^3$ represents a straight or branched C$_{1-6}$ alkylene chain.

8. A compound according to claim 1 wherein R$^2$ represents hydrogen.

9. A compound according to claim 1 wherein $L^1$ represents a methylene, ethylene or a straight or branched propylene linkage.

10. A compound according to claim 1 wherein Y represents carboxy.

11. A compound according to claim 1 selected from the following:

3-{7-[2-(2-o-tolylamino-benzoxazol-6-yl)-acetylamino]-indan-4-yl}-butyric acid;

{5-[2-(2-o-tolylamino-benzoxazol-6-yl)-acetylamino]-indan-2-yl}-acetic acid; and {5-[2-(2-o-tolylamino-benzoxazol-6-yl)-acetylamino]-indan-1-yl)-acetic acid; and the corresponding N-oxides, and their prodrugs; and pharmaceutically acceptable salts and solvates of such compounds and their N-oxides and prodrugs.

12. A compound according to claim 1 selected from the following:

ethyl 3-{7-[2-(2-o-tolylamino-benzoxazol-6-yl)-acetylamino]-indan-4-yl}-butanoate; and ethyl {5-[2-(2o-tolylamino-benzoxazol-6-yl)-acetylamino]-indan-1-yl}-acetate; and their N-oxides and prodrugs.

13. A compound according to claim 1 of formula (Ia);

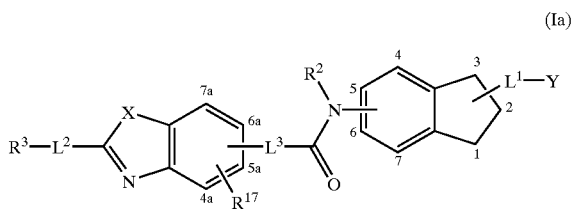

(Ia)

in which $R^2$, $R^3$, $L^1$, $L^2$, $L^3$ and Y are as defined in claim 1; X is O; and $R^{17}$ is hydrogen. alkoxy, halo or alkyl, and the corresponding N-oxides, and their prodrugs; and pharmaceutically acceptable salts and solvates of such compounds and their N-oxides and prodrugs.

14. A compound according to claim 1 of formula (Ib):

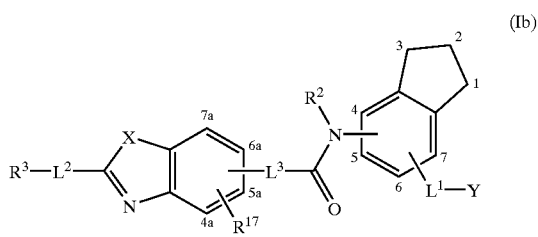

(Ib)

in which $R^2$, $R^3$, $L^1$, $L^2$, $L^3$ and Y are as defined in claim 1; X is O; and $R^{17}$ is hydrogen, alkoxy, halo or alkyl, and the corresponding N-oxides, and their prodrugs; and pharmaceutically acceptable salts and solvates of such compounds and their N-oxides and prodrugs.

15. A pharmaceutical composition comprising an effective amount of a compound according to claim 1 or a corresponding N-oxide, or a prodrug thereof, or a pharmaceutically acceptable salt or solvate of such a compound or its N-oxide or a prodrug thereof, in association with a pharmaceutically acceptable carrier or excipient.

16. A method for the treatment of a patient suffering from, or subject to, asthma comprising administering to said patient an effective amount of a compound according to claim 1 or a corresponding N-oxide or prodrug, or a pharmaceutically acceptable salt or solvate of such a compound or an N-oxide or prodrug thereof.

17. A method for the treatment of a patient suffering from, or subject to, an inflammatory disease comprising administering to said patient an effective amount of a compound according to claim 1 or a corresponding N-oxide or prodrug, or a pharmaceutically acceptable salt or solvate of such a compound or an N-oxide or prodrug thereof.

18. A method for the treatment of a patient suffering from, or subject to, asthma comprising administering to said patient an effective amount of a composition according to claim 15.

19. A method for the treatment of a patient suffering from, or subject to, an inflammatory disease comprising administering to said patient an effective amount of a composition according to claim 15.

* * * * *